(12) United States Patent
Wang et al.

(10) Patent No.: US 7,981,601 B2
(45) Date of Patent: Jul. 19, 2011

(54) METHOD OF PREPARING POLYEPITOPE CHIMERIC GENE VACCINE

(75) Inventors: Heng Wang, Beijing (CN); Qiliang Cai, Beijing (CN)

(73) Assignees: Institute of Basic Medical Sciences, Beijing (CN); Chinese Academy of Medical Sciences, Beijing (CN)

( * ) Notice: Subject to any disclaimer, the term of this patent is extended or adjusted under 35 U.S.C. 154(b) by 1073 days.

(21) Appl. No.: 10/566,697

(22) PCT Filed: Aug. 1, 2003

(86) PCT No.: PCT/CN03/00620
§ 371 (c)(1),
(2), (4) Date: May 10, 2006

(87) PCT Pub. No.: WO2005/012528
PCT Pub. Date: Feb. 10, 2005

(65) Prior Publication Data
US 2007/0009892 A1    Jan. 11, 2007

(51) Int. Cl.
*C12Q 1/28* (2006.01)
*C12P 21/02* (2006.01)

(52) U.S. Cl. ........... 435/6; 435/4; 435/2; 506/10; 506/9; 506/7; 424/9.322; 514/44

(58) Field of Classification Search ................. 435/6, 4, 435/2; 506/10, 9, 7; 424/9.322; 514/44
See application file for complete search history.

(56) References Cited

U.S. PATENT DOCUMENTS

| | | | |
|---|---|---|---|
| 6,291,214 B1 * | 9/2001 | Richards et al. | 435/91.4 |
| 6,602,510 B1 * | 8/2003 | Fikes et al. | 424/277.1 |
| 7,026,443 B1 * | 4/2006 | Sette et al. | 530/300 |

FOREIGN PATENT DOCUMENTS

| | | |
|---|---|---|
| EP | 0198328 A1 | 10/1986 |
| WO | 02064161 A2 | 8/2002 |

OTHER PUBLICATIONS

Lln et al, Chinese J. of Bochemistry, 1999, 15(6), 974-977.*
Ming et al, Chinese Medical Jrnl. 1999, 112(8), 691-697.*

Lin Chengtao, et al.,"Construction of Malaria Multivalent Recombinant DNA Vaccine with Isocaudamer Technique," Chinese Journal of Biochemistry and Molecular Biology, vol. 15, No. 6, 1999, pp. 974-977.
Yanfang I, et al., "Effects of the Configuration of a Multi-Epitope Chimeric Malaria DNA Vaccine on its Antigenicity to Mice" Chinese Medical Journal, vol. 112, No. 8, 1999, pp. 686-690.
Li Ming, et al, "A recombinant multi-epitope, multi-stage malaria vaccine candidate expressed in *Escherichia coli*," Chinese Medical Journal, vol. 112, No. 8, 1999, pp. 691-697.
Smooker P M, et al, "Expression library immunization protects mice against a challenge with virulent rodent malaria," Vaccine, vol. 18, No. 23, May 2000, pp. 2533-2540.
Doolan D L, et al., "DNA-based vaccines against malaria: status and promise of the Multi-Stage Malaria DNA Vaccine Operation," International Journal of Parasitology, GB, vol. 31, No. 8 Jun. 2001, pp. 753-762.
Tine J A, et al., "NYVAC-Pf7: a poxvirus-vectored, multiantigen, multistage vaccine candidate for *Plasmodium falciparum* malaria," Infection and Immunity, vol. 9, No. 64, Sep. 1996, pp. 3833-3844.
Cai Q-L, et al., "Immunogenicity of polyepitope libraries assembled by epitope shuffling: an approach to the development of chimeric gene vaccination against malaria" Vaccine, vol. 23, No. 2, Nov. 25, 2004, pp. 267-277.
Kumar Sanjai, et al. "A multilateral effort to develop DNA vaccines against falciparum malaria," Trends in Parasitiogy, vol. 18, No. 3, Mar. 2002, pp. 129-135.
Patten P A, et al.: "Applications of DNA Shuffling to Pharmaceuticals and Vaccines," Current Opinion in Biotechnology, vol. 8, 1997, pp. 724-733.
European Patent Office, Supplementary European Search Report for Appln. No. EP 03 81 7738, Sep. 18, 2006.
International Searching Authority/ China, International Search Report for Appln. No. PCT/CN03/00620 and English translation, Jun. 3, 2004, and English translation.

* cited by examiner

*Primary Examiner* — T. D. Wessendorf
(74) *Attorney, Agent, or Firm* — Paul & Paul

(57) ABSTRACT

The invention relates to a method for preparing polyepitope chimeric gene vaccines, designated as Epitopes Assemble Library Immunization (EALI). It involves the construction of expression libraries of polyepitope chimeric genes with different sizes and lengths using gene shuffling and random assembly so as to screen polyepitope chimeric gene vaccines. Immunization of the body with the gene libraries of the invention results in the induction of high level of specific antibodies and specific types of cytokines, and protection on the body.

18 Claims, 8 Drawing Sheets

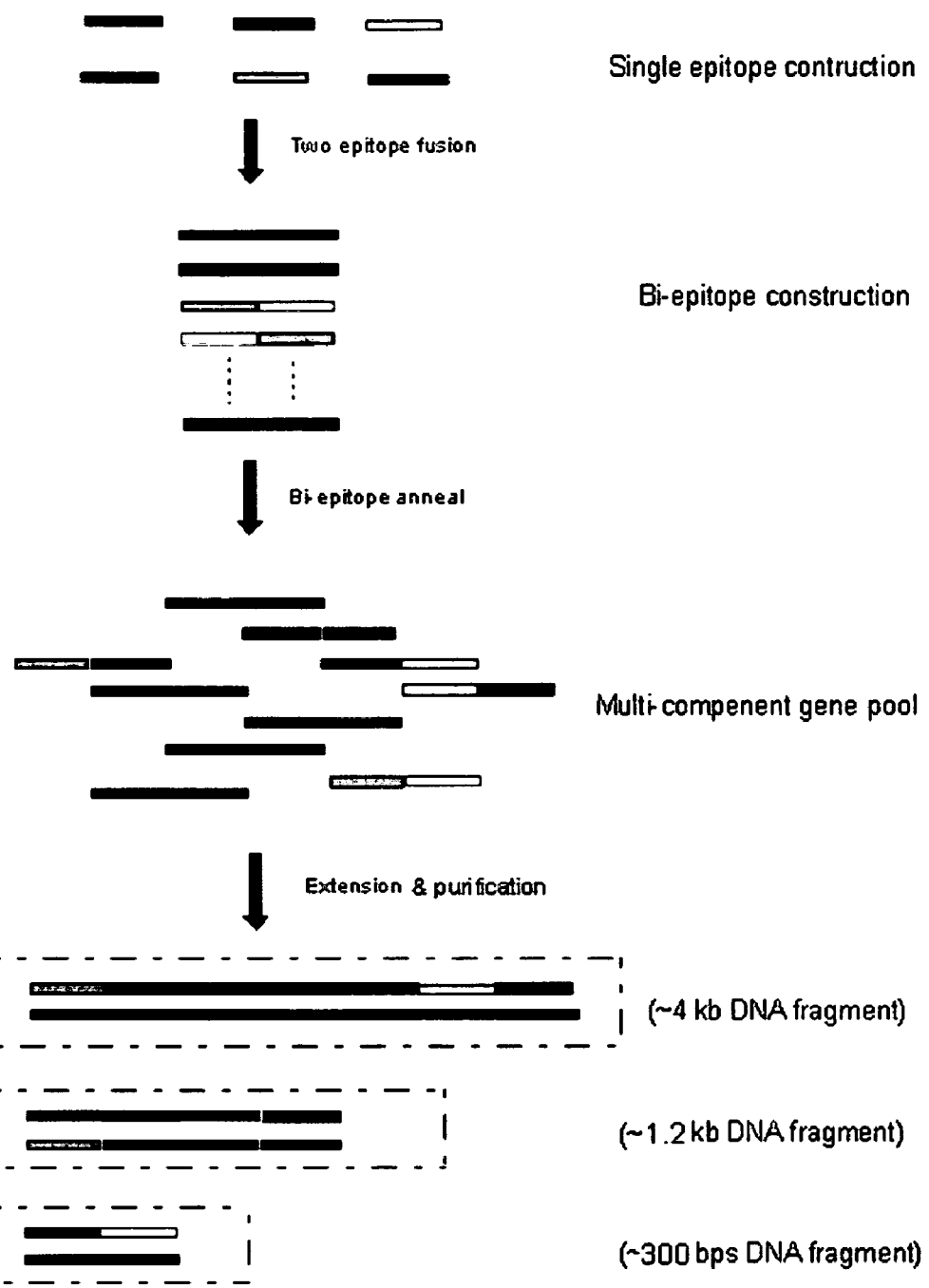
Fig. 1  Scheme of the random assembling of polyepitope genes with EALI

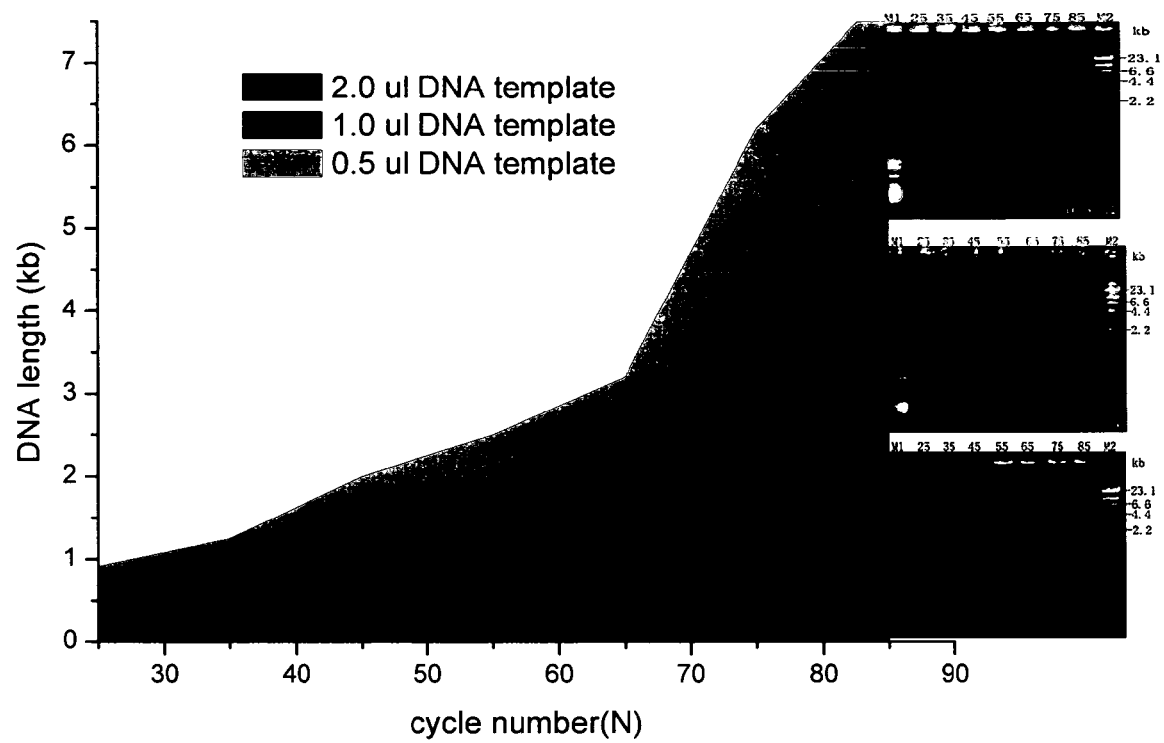
Fig. 2 Graph of polyepitope genes randomly constructed by using a primer-free polymerase chain reaction under different conditions

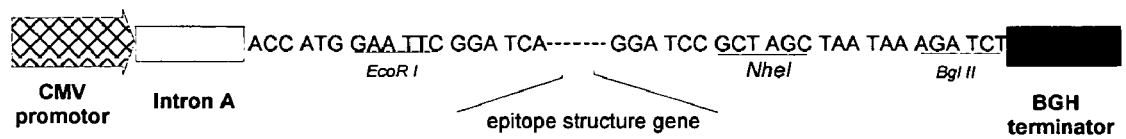
Fig. 3 Gene structure of a polyepitope gene vaccine in an eukaryotic expression vector
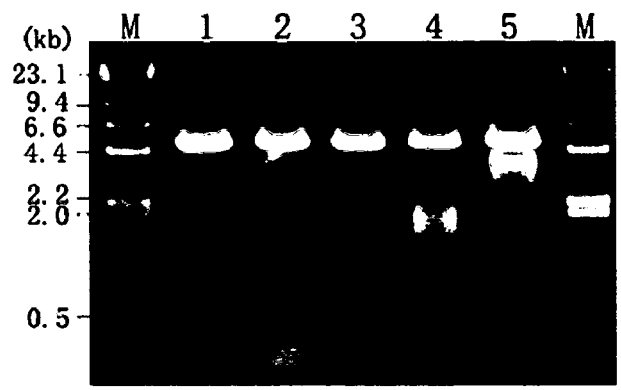
Figure 4 Gene lengths in different polyepitope chimeric gene libraries A
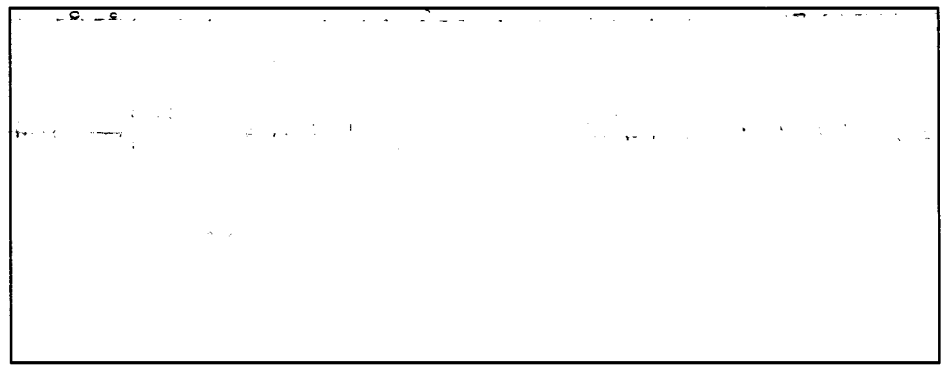
B
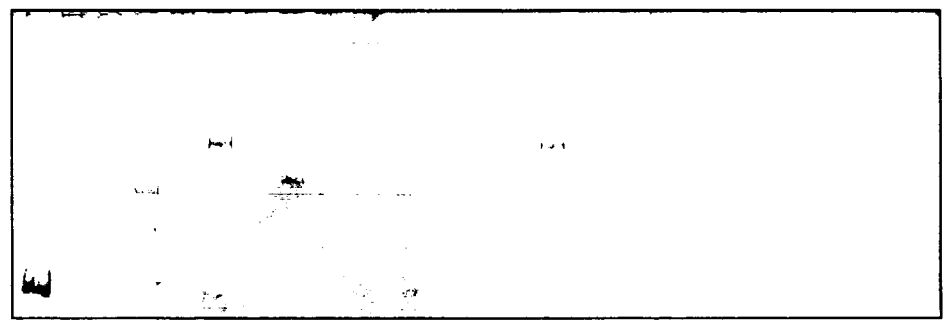
Figure 5 PCR-SSCP assay for the gene diversity of polyepitope chimeric gene libraries with different lengths

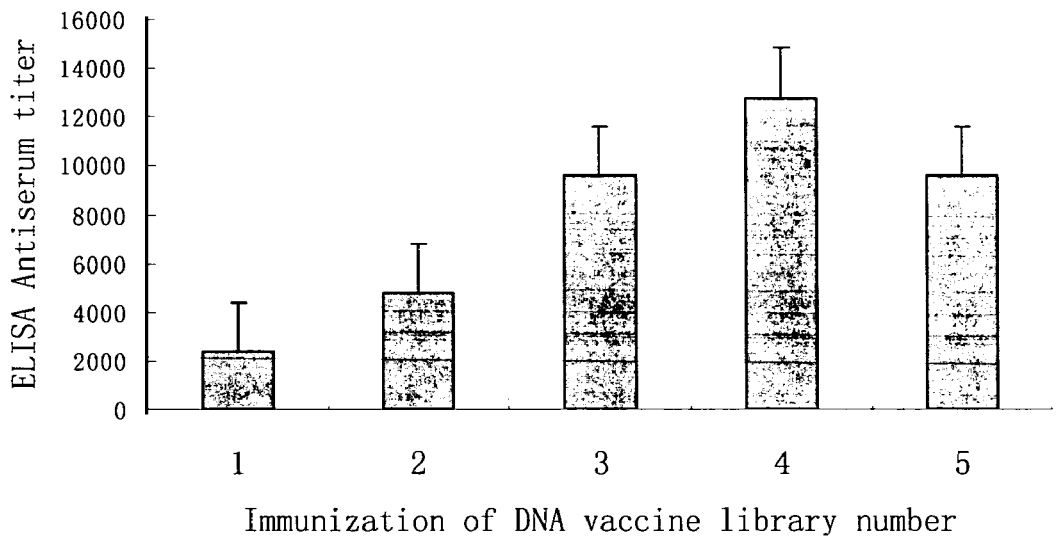
Figure 6 Antibody levels generated by the epitope gene libraries with different lengths
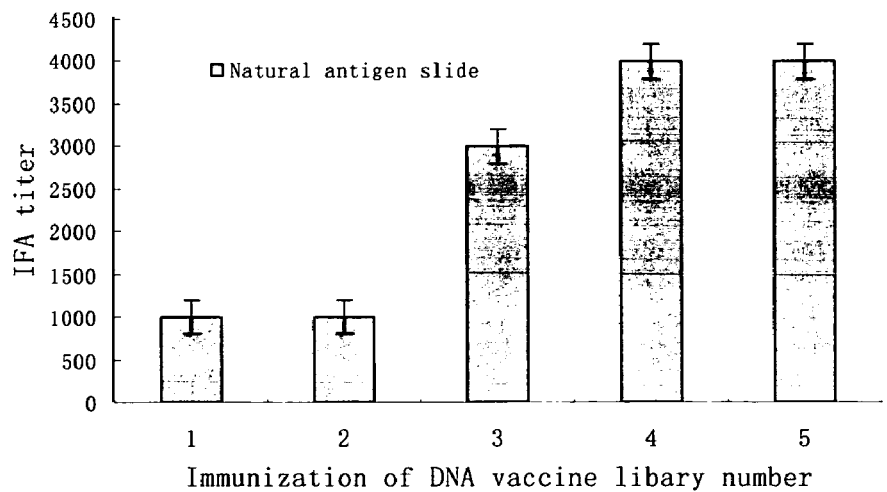
Figure 7 Recognition of native parasite antigens by dilutions of the antibodies generated by polyepitope gene libraries with different lengths

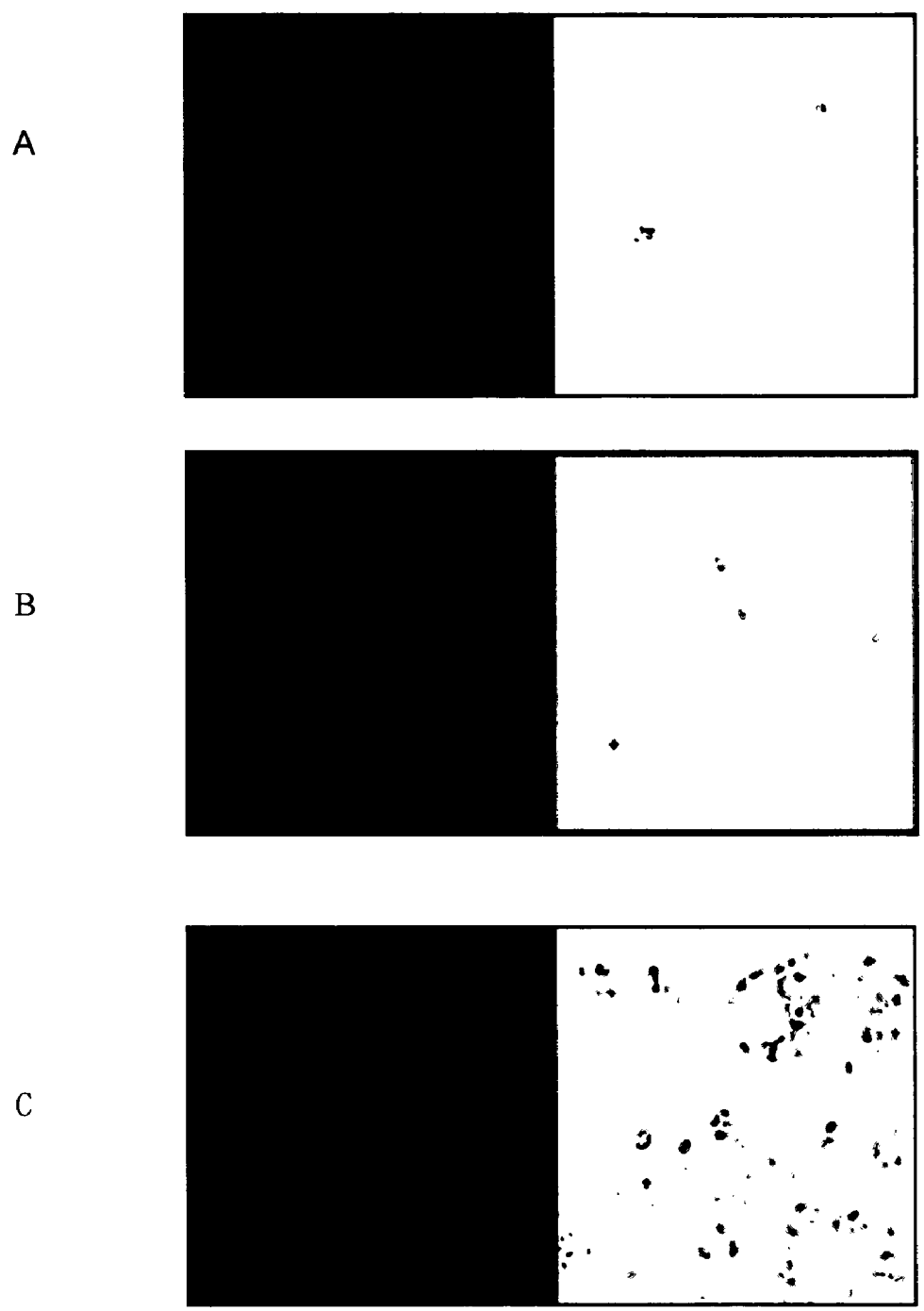
Figure 8  Confocal microscopy results showing the recognization of different native antigens of plasmodium by antibodies generated by polyepitope gene vaccines in No.4 library Figure 9 Western blot result demonstrating the recognition of native antigens of plasmodium strain 3D7 by antisera generated by the polyepitope chimeric gene vaccines in No. 3 library (3000× diluted)

Figure 10 Cross protection by the polyepitope chimeric gene vaccines in different libraries against *Plasmodium yoelii*

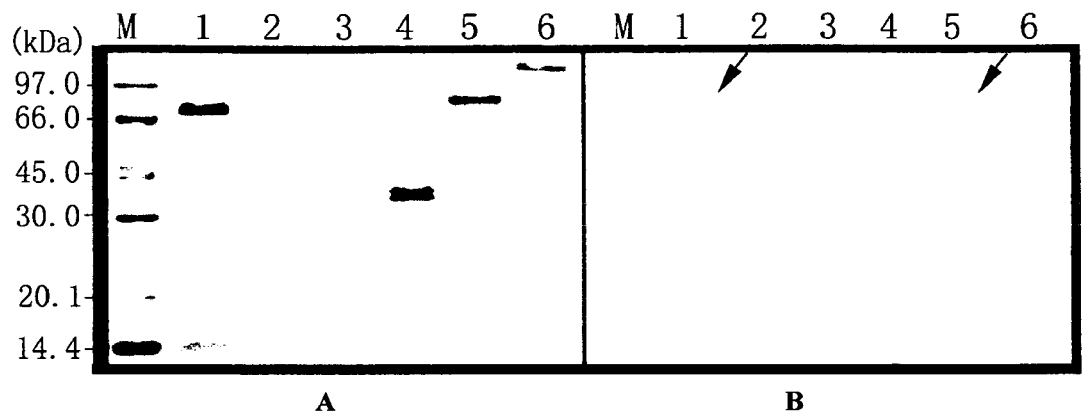
Figure 11 Western blot of the prokaryotic expression of antigen genes with high immunogenicity
A. SDS-PAGE; B. hybridization membrane
1. SP312; 2. vector; 3. SN33; 4. SN34; 5. SP352; 6. SN36.
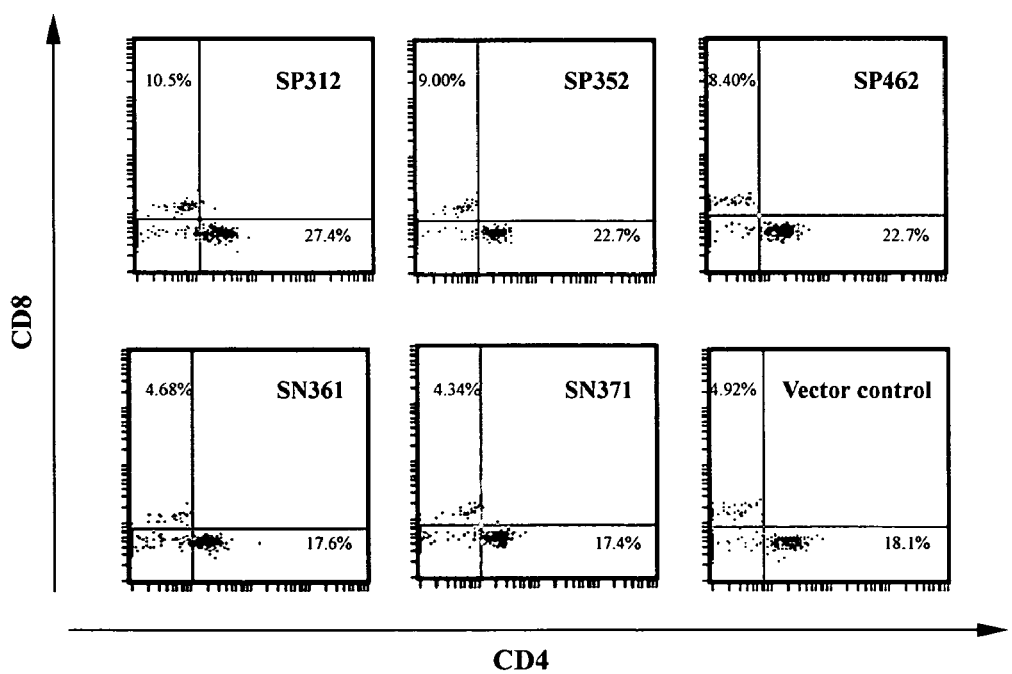
Figure 12 Detection of cytokines involved in in vivo immune response elicited by the positive (SP) and negative (SN) clones screened from the libraries

SEQUENCE LISTING

<160> NUMBER OF SEQ ID NOS: 53

<210> SEQ ID NO 1
<211> LENGTH: 4
<212> TYPE: PRT
<213> ORGANISM: Artificial sequence
<220> FEATURE:
<223> OTHER INFORMATION: Artificial peptide linker

<400> SEQUENCE: 1

Gly Pro Gly Pro
1

<210> SEQ ID NO 2
<211> LENGTH: 8
<212> TYPE: PRT
<213> ORGANISM: Plasmodium falciparum

<400> SEQUENCE: 2

Asn Lys Asn Asp Asn Lys Asn Asp
1               5

<210> SEQ ID NO 3
<211> LENGTH: 23
<212> TYPE: PRT
<213> ORGANISM: Plasmodium falciparum

<400> SEQUENCE: 3

Lys Asn Glu Ser Lys Tyr Ser Asn Thr Phe Ile Asn Asn Ala Tyr Asn
1               5                   10                  15

Met Ser Ile Arg Arg Ser Met
            20

<210> SEQ ID NO 4
<211> LENGTH: 8
<212> TYPE: PRT
<213> ORGANISM: Plasmodium falciparum

<400> SEQUENCE: 4

Glu Glu Asn Val Glu His Asp Ala
1               5

<210> SEQ ID NO 5

```
<211> LENGTH: 18
<212> TYPE: PRT
<213> ORGANISM: Plasmodium falciparum

<400> SEQUENCE: 5

Glu Arg Glu Asp Glu Arg Thr Leu Thr Lys Glu Tyr Glu Asp Ile Val
1               5                   10                  15

Leu Lys

<210> SEQ ID NO 6
<211> LENGTH: 20
<212> TYPE: PRT
<213> ORGANISM: Plasmodium falciparum

<400> SEQUENCE: 6

Leu Asp Asn Ile Lys Asp Asn Val Gly Lys Met Glu Asp Tyr Ile Lys
1               5                   10                  15

Lys Asn Lys Lys
            20

<210> SEQ ID NO 7
<211> LENGTH: 18
<212> TYPE: PRT
<213> ORGANISM: Plasmodium falciparum

<400> SEQUENCE: 7

Glu Gln Gln Ser Asp Leu Glu Gln Glu Arg Leu Arg Ala Lys Glu Lys
1               5                   10                  15

Leu Gln

<210> SEQ ID NO 8
<211> LENGTH: 15
<212> TYPE: PRT
<213> ORGANISM: Plasmodium falciparum

<400> SEQUENCE: 8

Lys Lys Ile Ala Lys Met Glu Lys Ala Ser Ser Val Phe Asn Val
1               5                   10                  15

<210> SEQ ID NO 9
<211> LENGTH: 18
<212> TYPE: PRT
<213> ORGANISM: Plasmodium falciparum

<400> SEQUENCE: 9

Asn Ser Gly Cys Phe Arg His Leu Asp Glu Arg Glu Glu Cys Lys Cys
1               5                   10                  15

Leu Leu

<210> SEQ ID NO 10
<211> LENGTH: 19
<212> TYPE: PRT
<213> ORGANISM: Plasmodium falciparum

<400> SEQUENCE: 10

Glu Asp Ser Gly Ser Asn Gly Lys Lys Ile Thr Cys Glu Cys Thr Lys
1               5                   10                  15

Pro Asp Ser

<210> SEQ ID NO 11
<211> LENGTH: 19
<212> TYPE: PRT
<213> ORGANISM: Plasmodium falciparum
```

<400> SEQUENCE: 11

Asp Gly Asn Cys Glu Asp Ile Pro Ile Ile Val Asn Glu Phe Ser Ala
1               5                   10                  15
Ile Asp Leu

<210> SEQ ID NO 12
<211> LENGTH: 18
<212> TYPE: PRT
<213> ORGANISM: Plasmodium falciparum

<400> SEQUENCE: 12

Gly Asn Ala Glu Lys Tyr Asp Lys Met Asp Glu Pro Gln His Tyr Gly
1               5                   10                  15
Lys Ser

<210> SEQ ID NO 13
<211> LENGTH: 19
<212> TYPE: PRT
<213> ORGANISM: Plasmodium falciparum

<400> SEQUENCE: 13

Asp Gln Pro Lys Gln Tyr Glu Gln His Leu Thr Asp Tyr Glu Lys Ile
1               5                   10                  15
Lys Glu Gly

<210> SEQ ID NO 14
<211> LENGTH: 17
<212> TYPE: PRT
<213> ORGANISM: Plasmodium falciparum

<400> SEQUENCE: 14

Gly Ile Ser Tyr Tyr Glu Lys Val Leu Ala Lys Tyr Lys Asp Asp Leu
1               5                   10                  15
Glu

<210> SEQ ID NO 15
<211> LENGTH: 10
<212> TYPE: PRT
<213> ORGANISM: Plasmodium falciparum

<400> SEQUENCE: 15

Gln Thr Asp Glu Ile Lys Asn Asp Asn Ile
1               5                   10

<210> SEQ ID NO 16
<211> LENGTH: 17
<212> TYPE: DNA
<213> ORGANISM: Artificial sequence
<220> FEATURE:
<223> OTHER INFORMATION: Artificial oligonucleotide primer

<400> SEQUENCE: 16
gatcaccatg gaattcg                                                17

<210> SEQ ID NO 17
<211> LENGTH: 17
<212> TYPE: DNA
<213> ORGANISM: Artificial sequence
<220> FEATURE:
<223> OTHER INFORMATION: Artificial oligonucleotide primer

<400> SEQUENCE: 17

```
gatccgaatt ccatggt                                               17
```

<210> SEQ ID NO 18
<211> LENGTH: 32
<212> TYPE: DNA
<213> ORGANISM: Artificial sequence
<220> FEATURE:
<223> OTHER INFORMATION: Artificial oligonucleotide primer

<400> SEQUENCE: 18

```
acatcatgcc tgatcaaaca agaacgacaa ca                              32
```

<210> SEQ ID NO 19
<211> LENGTH: 32
<212> TYPE: DNA
<213> ORGANISM: Artificial sequence
<220> FEATURE:
<223> OTHER INFORMATION: Artificial oligonucleotide primer

<400> SEQUENCE: 19

```
tgttcttgct gttgttcttg ctgcctaggc gc                              32
```

<210> SEQ ID NO 20
<211> LENGTH: 36
<212> TYPE: DNA
<213> ORGANISM: Artificial sequence
<220> FEATURE:
<223> OTHER INFORMATION: Artificial oligonucleotide primer

<400> SEQUENCE: 20

```
acatcatgcc tgatcaaaga acgagagcaa gtacag                          36
```

<210> SEQ ID NO 21
<211> LENGTH: 40
<212> TYPE: DNA
<213> ORGANISM: Artificial sequence
<220> FEATURE:
<223> OTHER INFORMATION: Artificial oligonucleotide primer

<400> SEQUENCE: 21

```
gctctcgttc atgtcgttgt ggaagtagtt gttgcggatg                      40
```

<210> SEQ ID NO 22
<211> LENGTH: 41
<212> TYPE: DNA
<213> ORGANISM: Artificial sequence
<220> FEATURE:
<223> OTHER INFORMATION: Artificial oligonucleotide primer

<400> SEQUENCE: 22

```
catcaacaac gcctacaaca tgagcatccg ccgcagcatg g                    41
```

<210> SEQ ID NO 23
<211> LENGTH: 34
<212> TYPE: DNA
<213> ORGANISM: Artificial sequence
<220> FEATURE:
<223> OTHER INFORMATION: Artificial oligonucleotide primer

<400> SEQUENCE: 23

```
ggcggcgtcg tacccggggc cggggcctag gcgc                            34
```

<210> SEQ ID NO 24
<211> LENGTH: 32
<212> TYPE: DNA
<213> ORGANISM: Artificial sequence
<220> FEATURE:

<223> OTHER INFORMATION: Artificial oligonucleotide primer

<400> SEQUENCE: 24
acatcatgcc tgatcagagg agaacgtgga gc                32

<210> SEQ ID NO 25
<211> LENGTH: 32
<212> TYPE: DNA
<213> ORGANISM: Artificial sequence
<220> FEATURE:
<223> OTHER INFORMATION: Artificial oligonucleotide primer

<400> SEQUENCE: 25
tcctcttgca cctcgtgctg cggcctaggc gc                32

<210> SEQ ID NO 26
<211> LENGTH: 53
<212> TYPE: DNA
<213> ORGANISM: Artificial sequence
<220> FEATURE:
<223> OTHER INFORMATION: Artificial oligonucleotide primer

<400> SEQUENCE: 26
acatcatgcc tgatcagagc gcgaggacga gcgcaccctg accaaggagt acg                53

<210> SEQ ID NO 27
<211> LENGTH: 54
<212> TYPE: DNA
<213> ORGANISM: Artificial sequence
<220> FEATURE:
<223> OTHER INFORMATION: Artificial oligonucleotide primer

<400> SEQUENCE: 27
gactggttcc tcatgctcct gtagcacgac ttcccggggc cggggcctag gcgc                54

<210> SEQ ID NO 28
<211> LENGTH: 43
<212> TYPE: DNA
<213> ORGANISM: Artificial sequence
<220> FEATURE:
<223> OTHER INFORMATION: Artificial oligonucleotide primer

<400> SEQUENCE: 28
acatcatgcc tgatcactgg acaacatcaa ggacaacgtg ggc                43

<210> SEQ ID NO 29
<211> LENGTH: 42
<212> TYPE: DNA
<213> ORGANISM: Artificial sequence
<220> FEATURE:
<223> OTHER INFORMATION: Artificial oligonucleotide primer

<400> SEQUENCE: 29
tcctgttgca cccgttctac ctcctgatgt agttcttctt gt                42

<210> SEQ ID NO 30
<211> LENGTH: 41
<212> TYPE: DNA
<213> ORGANISM: Artificial sequence
<220> FEATURE:
<223> OTHER INFORMATION: Artificial oligonucleotide primer

<400> SEQUENCE: 30
tacatcaaga agaacaagaa gggccccggc cccggatccg c                41

<210> SEQ ID NO 31

```
<211> LENGTH: 32
<212> TYPE: DNA
<213> ORGANISM: Artificial sequence
<220> FEATURE:
<223> OTHER INFORMATION: Artificial oligonucleotide primer

<400> SEQUENCE: 31
cggggcctag gcgatcgatt atttctagaa gg                          32

<210> SEQ ID NO 32
<211> LENGTH: 50
<212> TYPE: DNA
<213> ORGANISM: Artificial sequence
<220> FEATURE:
<223> OTHER INFORMATION: Artificial oligonucleotide primer

<400> SEQUENCE: 32
acatcatgcc tgatcagagc agcagagcga cctggagcag gagcgcctgg        50

<210> SEQ ID NO 33
<211> LENGTH: 51
<212> TYPE: DNA
<213> ORGANISM: Artificial sequence
<220> FEATURE:
<223> OTHER INFORMATION: Artificial oligonucleotide primer

<400> SEQUENCE: 33
gtcctcgcgg accggttcct cttcgacgtc ccggggccgg ggcctaggcg c      51

<210> SEQ ID NO 34
<211> LENGTH: 49
<212> TYPE: DNA
<213> ORGANISM: Artificial sequence
<220> FEATURE:
<223> OTHER INFORMATION: Artificial oligonucleotide primer

<400> SEQUENCE: 34
acatcatgcc tgatcaaaga agatcgccaa gatggagaag gccagcagc         49

<210> SEQ ID NO 35
<211> LENGTH: 48
<212> TYPE: DNA
<213> ORGANISM: Artificial sequence
<220> FEATURE:
<223> OTHER INFORMATION: Artificial oligonucleotide primer

<400> SEQUENCE: 35
ctcttccggt cgtcgcacaa gttgcacccg gggccggggc ctaggcgc          48

<210> SEQ ID NO 36
<211> LENGTH: 49
<212> TYPE: DNA
<213> ORGANISM: Artificial sequence
<220> FEATURE:
<223> OTHER INFORMATION: Artificial oligonucleotide primer

<400> SEQUENCE: 36
acatcatgcc tgatcaaaca gcggctgctt ccgccacctg gacgagcgc         49

<210> SEQ ID NO 37
<211> LENGTH: 44
<212> TYPE: DNA
<213> ORGANISM: Artificial sequence
<220> FEATURE:
<223> OTHER INFORMATION: Artificial oligonucleotide primer

<400> SEQUENCE: 37
```

```
tggacctgct cgcgctcctc acgttcacgg acgaccctag gcgc              44
```

<210> SEQ ID NO 38
<211> LENGTH: 52
<212> TYPE: DNA
<213> ORGANISM: Artificial sequence
<220> FEATURE:
<223> OTHER INFORMATION: Artificial oligonucleotide primer

<400> SEQUENCE: 38

```
acatcatgcc tgatcagagg acagcggcag caacggcaag aagatcacct gc      52
```

<210> SEQ ID NO 39
<211> LENGTH: 46
<212> TYPE: DNA
<213> ORGANISM: Artificial sequence
<220> FEATURE:
<223> OTHER INFORMATION: Artificial oligonucleotide primer

<400> SEQUENCE: 39

```
gttcttctag tggacgctca cgtggttcgg cctgtcgcct aggcgc             46
```

<210> SEQ ID NO 40
<211> LENGTH: 49
<212> TYPE: DNA
<213> ORGANISM: Artificial sequence
<220> FEATURE:
<223> OTHER INFORMATION: Artificial oligonucleotide primer

<400> SEQUENCE: 40

```
acatcatgcc tgatcagacg gcaactgcga ggacatcccg cacgtgaac          49
```

<210> SEQ ID NO 41
<211> LENGTH: 45
<212> TYPE: DNA
<213> ORGANISM: Artificial sequence
<220> FEATURE:
<223> OTHER INFORMATION: Artificial oligonucleotide primer

<400> SEQUENCE: 41

```
tagggcgtgc acttgctcaa gtcgcggtag ctggacccta ggcgc              45
```

<210> SEQ ID NO 42
<211> LENGTH: 52
<212> TYPE: DNA
<213> ORGANISM: Artificial sequence
<220> FEATURE:
<223> OTHER INFORMATION: Artificial oligonucleotide primer

<400> SEQUENCE: 42

```
acatcatgcc tgatcaggca acgccgagaa gtacgacaag atggacgagc cg      52
```

<210> SEQ ID NO 43
<211> LENGTH: 42
<212> TYPE: DNA
<213> ORGANISM: Artificial sequence
<220> FEATURE:
<223> OTHER INFORMATION: Artificial oligonucleotide primer

<400> SEQUENCE: 43

```
ttctacctgc tcggcgtcgt gatgccgttc tcgcctaggc gc                 42
```

<210> SEQ ID NO 44
<211> LENGTH: 52
<212> TYPE: DNA
<213> ORGANISM: Artificial sequence
<220> FEATURE:

<223> OTHER INFORMATION: Artificial oligonucleotide primer

<400> SEQUENCE: 44
acatcatgcc tgatcagacc agccgaagca gtacgagcag cacctgaccg ac        52

<210> SEQ ID NO 45
<211> LENGTH: 45
<212> TYPE: DNA
<213> ORGANISM: Artificial sequence
<220> FEATURE:
<223> OTHER INFORMATION: Artificial oligonucleotide primer

<400> SEQUENCE: 45
gtcgtggact ggctgatgct cttctagttc ctcccgccta ggcgc        45

<210> SEQ ID NO 46
<211> LENGTH: 49
<212> TYPE: DNA
<213> ORGANISM: Artificial sequence
<220> FEATURE:
<223> OTHER INFORMATION: Artificial oligonucleotide primer

<400> SEQUENCE: 46
acatcatgcc tgatcaggca tcagctacta cgagaaggtg ctggccaag        49

<210> SEQ ID NO 47
<211> LENGTH: 42
<212> TYPE: DNA
<213> ORGANISM: Artificial sequence
<220> FEATURE:
<223> OTHER INFORMATION: Artificial oligonucleotide primer

<400> SEQUENCE: 47
ttccacgacc ggttcatgtt cctgctggac ctccctaggc gc        42

<210> SEQ ID NO 48
<211> LENGTH: 55
<212> TYPE: DNA
<213> ORGANISM: Artificial sequence
<220> FEATURE:
<223> OTHER INFORMATION: Artificial oligonucleotide primer

<400> SEQUENCE: 48
acatcatgcc tgatcacaga ccgacgagat caagaacgac cacatccaga ccgat        55

<210> SEQ ID NO 49
<211> LENGTH: 45
<212> TYPE: DNA
<213> ORGANISM: Artificial sequence
<220> FEATURE:
<223> OTHER INFORMATION: Artificial oligonucleotide primer

<400> SEQUENCE: 49
gtgtaggtct ggctacttta attttacta ttataaccta ggcgc        45

<210> SEQ ID NO 50
<211> LENGTH: 18
<212> TYPE: DNA
<213> ORGANISM: Artificial sequence
<220> FEATURE:
<223> OTHER INFORMATION: Artificial oligonucleotide primer

<400> SEQUENCE: 50
ccagacataa tagctgac        18

<210> SEQ ID NO 51

-continued

```
<211> LENGTH: 18
<212> TYPE: DNA
<213> ORGANISM: Artificial sequence
<220> FEATURE:
<223> OTHER INFORMATION: Artificial oligonucleotide primer

<400> SEQUENCE: 51
gatggctggc aactagaa                                              18

<210> SEQ ID NO 52
<211> LENGTH: 16
<212> TYPE: DNA
<213> ORGANISM: Artificial sequence
<220> FEATURE:
<223> OTHER INFORMATION: Artificial oligonucleotide primer

<400> SEQUENCE: 52
acatcatgcc tgatca                                                16

<210> SEQ ID NO 53
<211> LENGTH: 15
<212> TYPE: DNA
<213> ORGANISM: Artificial sequence
<220> FEATURE:
<223> OTHER INFORMATION: Artificial oligonucleotide primer

<400> SEQUENCE: 53
ttagctagcg gatcc                                                 15
```

METHOD OF PREPARING POLYEPITOPE CHIMERIC GENE VACCINE

TECHNICAL FIELD

The present invention relates to a new method for artificially producing gene vaccines, designated as Epitopes Assemble Library Immunization (EALI). The method of the invention generally involves the construction of expression libraries of polyepitope chimeric genes with different sizes and lengths using epitope gene shuffling and random assembly so as to screen polyepitope chimeric gene vaccines.

BACKGROUND ART

Since the DNA shuffling technique developed by Stemmer was published in Science in 1994, many molecular breeding technologies relating to the artificial evolution of genes have been developed (Juha P. Int Arch Allergy Immunology. 121, 173-182 (2000)), including various improved protocols of gene shuffling (Huimin Z. et al. Nucleic Acids Research, 25 (6), 1307-1308 (1997); Andreas C. et al. Nature, 391 (15), 288-291 (1998); Miho K. et al. Gene, 236, 159-167 (1997)), staggered extension process (Huimin 7. et al. Nature Biotechnology, 16, 258-261 (1998)), incremental truncation for the creation of hybrid enzymes (Marc 0. et al. Nature Biotechnology, 17, 1205-1209 (1999)) and random chimeragenesis on transient templates (Wayne M C. et al. Nature Biotechnology, 19, 354-359 (2001)) etc. To date there are many successful examples in which the basic principles of the molecular evolution techniques have been applied to generate or modify genes in fields ranging from the common biological proteases to improvement of antibiotic titre, the degradation of pollutants in the environment, the reconstruction of viruses, and the development of pharmaceuticals. But it is rarely employed in field of DNA vaccines which is the third generation of human vaccines. Although many experts predict that the success of gene shuffling technology in gene vaccines will make it widely applicable to diseases such as cancer, autoimmune diseases and infectious diseases which severely harm human health (Dewey D. Y. R et al. Biotechnology Progress, 16 (1), 2-16 (2000); Phillip A P. et al. Current Opinion in Biotechnology, 8, 724-733 (1997); Robert G. W. et al. Curr Opin Mol Ther, 3 (1), 31-36 (2001)), there is no related literature or patents demonstrating substantial progress.

Gene vaccines represent a new immunological theory and technique developed in the 1990s and are the third generation of vaccines after attenuated virus vaccines and subunit vaccines (Wolff J. A. et al. Science, 247, 1465-8 (1990)). The technology of gene vaccines comprises the step of direct injection of plasmid DNA containing exogenous protein coding sequences into the body so as to enable the direct expression of the exogenous proteins in the body thereby eliciting an immune response. Gene vaccines have many advantages compared to conventional vaccines, such as prolonged immune response, simultaneous induction of humoral immunity and cytotoxic T cell response, simple preparation, convenience, inexpensive, stable antigen and convenient delivery, and so on. It not only has the safety proved by recombinant subunit vaccines and the high efficiency of attenuated virus vaccines for the induction of a general immune response but also elicits specific types of immune response in the body. Up to now, gene vaccines have been widely used for therapy of infectious diseases and cancer caused by viruses, bacteria and protozoa as well as in the therapy of allergic response and tolerance in new born infants. There is beneficial development in the therapy against influenza, AIDS, rabies, hepatitis B, tuberculosis, malaria and leishmaniosis (Lai W. C. et al. Crit. Rev Immunol, 18 (5), 449-84 (1998)). With respect to *plasmodium*, HIV and other highly variable viruses severely affecting human health, there are no very effective vaccines. For pathogens with highly variable properties, vaccine studies indicate that it is necessary to employ various antigens at various periods (Doolan D. L. et al. Int J Parasitol, 31 (8), 753-62 (2001)). For multiple antigen vaccines, many reports and patents have been published, which focus on single synthetic or recombinant vaccines of multiple antigens and polyepitope protein vaccines or the combination of limited types of such synthetic or recombinant vaccines. Moreover, it is problem that the synthesis of polypeptide vaccines is very costly, which hampers its practical application. Now some references report polyepitope chimeric gene vaccines, but the attention concentrates on the artificial and single chimeric pattern among polyepitope genes, and no immunoprotective effect better than that of polypeptide vaccine has been achieved. In view that three antigenic epitopes of *Plasmodium falciparum* (MSA-1, NKND and CST3) were selected during construction of a multivalent recombinant DNA vaccine, the inventors of the present invention carried out different construction and combination of polyepitope genes according to the combination pattern designed in advance and found that there was an optimal assembly in polyepitope combination (Lin C. T. Chinese J of Biochemistry and Molecular Biology, 1999, 15 (6): 974-977). The result indicated that with respect to the combination of a few epitopes (less than 3), the optimal combination may be obtained by manually individual assembly and construction. But as the combination of more epitopes (more than 3) provides many possibilities, it is impractical to assemble and construct by the above method because it is complicated, costly and requires much work. Thus, how to effectively design polyepitope genes and overcome the variability of pathogens is required for the development of gene vaccines (Yu Z. et al. Vaccine, 16 (7), 1660-7 (1998); Kumar S. et al. Trends Parasitol, 18 (3), 129-35 (2002); Hoffman S. L. et al. Dev Biol, 104, 121-32 (2000); Li M. et al. Chin Med J (Engl), 112 (8), 691-7 (1999); Jiang Y. et al. Chin Med J (Engl), 112 (8), 686-90 (1999)).

The life cycle of *Plasmodium falciparum* which causes malignant malaria severely affecting human health is complicated and comprises four stages comprising asexual reproduction and sexual reproduction in humans and sexual reproduction and sporogony in mosquitoes. In humans there are exoerythrocytic (liver) and erythrocytic stages, while gametocyte and sporozoite stages are in mosquitoes. Such complex biological traits cause *Plasmodium falciparum* to have highly variable response against the immunoprotection of the host and drugs, so that single protective antigenic vaccines against malaria are not effective.

The clinical symptoms caused by *plasmodium* are mainly due to its asexual reproduction in the red blood cells of the host. Erythrocytic stage vaccines are designed to act directly against this unique pathogenic stage of *plasmodium*. Malaria vaccines comprise attenuated circumsporozoite vaccine, subunit vaccine and synthetic peptide vaccine, but they are not successful because the various antigens against which various vaccines are directed can not generate satisfactory protective effects. Therefore, it is well accepted in the art that the combination of multi-stage and multivalent epitopes is necessary in the construction of a malaria vaccine, to make it possible to obtain the desired protective effect. However, it is difficult to determine the quantity and linking order of the genes encoding polypeptides during the construction of multi-stage and multivalent vaccines manually, and the induction of humoral immunity by epitope DNA vaccines is generally not satisfactory, which are problems to be solved.

SUMMARY OF THE INVENTION

In one aspect of the present invention, a method for preparing polyepitope chimeric gene vaccines is provided, in which gene recombination in random libraries is used to construct new gene vaccines, comprising the steps of:
  a) selecting, synthesizing and cloning into a vector a plurality of nucleic acid molecules each encoding a single epitope of an antigen of interest;
  b) constructing nucleic acid molecules encoding randomly combined bi-epitopes in the vectors of step a) by isocaudamer linkage;
  c) randomly assembling polyepitope chimeric genes with different lengths from the nucleic acid molecules encoding bi-epitopes of step b);
  d) isolating, purifying and amplifying polyepitope chimeric genes according to different length ranges, then subcloning them into expression vectors and transforming prokaryotic hosts, respectively to obtain polyepitope chimeric gene expression libraries in the corresponding length ranges;
  e) detecting differences of polyepitope chimeric genes in each expression library to ensure the high diversity of the gene libraries;
  f) immunizing animals with each polyepitope chimeric gene library, then detecting the immunogenicity of expression products of genes in the polyepitope chimeric gene libraries;
  g) determining one or more gene libraries containing optimally assembled polyepitope chimeric gene vaccines according to the results of step e) and f);
  h) screening polyepitope chimeric gene vaccines with high immunogenicity from gene libraries obtained in step g) by high-throughput immunochemistry methods.

In another aspect, the present invention provides a method for preparing polyepitope chimeric gene vaccines, comprising the steps of:
  a) selecting, synthesizing and cloning Into a vector a plurality of nucleic acid molecules each encoding a single epitope of an antigen of interest;
  b) constructing nucleic acid molecules encoding randomly combined bi-epitopes in the vectors of step a) by isocaudamer linkage;
  c) randomly assembling polyepitope chimeric genes with different lengths from the nucleic acid molecules encoding bi-epitopes of step b);
  d) selecting polyepitope chimeric genes according to different length ranges, cloning the polyepitope chimeric genes into expression vectors to obtain polyepitope chimeric gene expression libraries in the corresponding length ranges;
  e) detecting differences of polyepitope chimeric genes in the polyepitope chimeric gene expression libraries to ensure the high diversity of the gene libraries used for vaccines.

According to the method of the present invention, the random assembling of polyepitope chimeric genes with different lengths in step c) is carried out simultaneously by following two methods to increase the randomization of tandem recombinations of different epitopes: 1) combined polymerase chain reaction and primer-free polymerase chain reaction; and 2) random linkage using isocaudamer sites in the vector.

According to one aspect of the present invention, the invention provides a polyepitope chimeric gene vaccine prepared by the method of the invention. In one embodiment of the invention, said polyepitope chimeric gene vaccine is a polyepitope chimeric gene vaccine directed against *Plasmodium falciparum*.

DESCRIPTION OF FIGURES

FIG. 1 is a scheme showing the random assembling of polyepitope genes. In the figure, 1: obtaining some single epitope genes, 2: constructing bi-epitopes by random assembling, 3: primer-free polymerase chain reaction; 4: isolation and purification of DNA fragments of different sizes and establishment of chimeric gene libraries.

FIG. 2 shows a graph of polyepitope genes randomly constructed by using a primer-free polymerase chain reaction under different conditions, obtained as follow: using the mixture of random assembled bi-epitope genes as templates (in the concentration of 0.5 μl/μl, 0.5 μl, 1.0 μl, and 2.0 μl, respectively), and in a 50 μl system primer-free polymerase chain reaction was carried out for cycles of 25, 35, 45, 55, 65, 75, and 85, respectively. The result indicated when the amount of the templates was less than 0.5 μl (250 ng), as the number of cycles increased, the size of the main products of the amplification was increasing. When the cycles of 65-75 were used, the length may be about 2 kb, and when more than 85 cycles, the fragment was larger than 4 kb.

FIG. 3 shows the gene structure of a polyepitope chimeric gene vaccine in an eukaryotic expression vector. For gene expression analysis, a common epitope sequence (e.g. $E6_{(MSA-1)}$) may be inserted downstream of each polyepitope gene.

FIG. 4 shows the length comparison of genes in different polyepitope chimeric gene libraries, in which M, λ/HindIII; 1, genes in No. 1 library/EcoRI+Bg/II; 2, genes in No. 2 library/EcoRI+Bg/II; 3, genes in No. 3 library/EcoRI+Bg/II; 4, genes in No. 4 library/EcoRI+Bg/II; 5, genes in No. 5 library/EcoRI+Bg/II.

FIG. 5 shows the diversity analysis of genes in polyepitope chimeric gene libraries with different lengths.

A. shows that the structural diversity of genes in the No. 3 gene library is 96% (24/25); B. indicating the structural diversity of genes in the No. 4 gene library is 100% (25/25). 25 recombinant clones selected randomly from both libraries were used to perform PCR with primers downstream and upstream of the multiple cloning sites of vector VR1012. The products of amplification were denatured at 100° C. for 10 min, placed on ice for 10 min, and then mixed with 10× sample buffer for polyacrylamide gel electrophoresis (10%) to analyze the difference between the bands.

FIG. 6 shows the level of antibodies in mice immunized with the mixed polyepitope chimeric gene vaccines of libraries with different lengths. Eight epitopes ($E2_{(NKND)}$, $E3_{(MSA-2)}$, $E5_{(EBA-175)}$, $E6_{(MSA-1)}$, $E7_{(LSA-1)}$, $E8_{(CS.T3/CSP)}$, $E9_{(MSP-1)}$ and $E11_{(AMA-1)}$) were mixed to coat microplates with 200 ng/well. Five mixed gene libraries were used to immunize Balb/c mice at 100 μg DNA with Dendrimer PAMAN G9 (1:6.5, w/w) in order to generate antisera. The antisera were then 2× diluted to measure the value at $OD_{450}$. The positive has a value at least two folds of that of the control.

FIG. 7 shows the IFA detection of the dilutions of the corresponding antibodies generated by mixed polyepitope chimeric gene vaccines in the libraries with different lengths.

Five gene libraries were used to immunize Balb/c mice twice at 100 μg DNA to generate antisera, which were 2× diluted. The negative control was used as a reference, and the positive has a fluorescence intensity significantly different from that of the control.

FIG. 8 shows the confocal microscopy results that the antibodies against mixed epitope gene vaccines in No. 4 library recognize different native antigens of *plasmodium*.

A. A blood smear of *Plasmodium falciparfum* 3D7; B. A blood smear of *Plasmodium falciparfum* FCC1; C. A blood smear of *Plasmodium yoelii*.

FIG. 9 shows a Western blot result demonstrating that the corresponding antisera against the mixed polyepitope chimeric gene vaccines in No. 3 library recognize native antigens of *plasmodium* strain 3D7.

1. The culture of strain 3D7 not treated with Spanin; 2. The culture of strain 3D7 treated with Spanin; 3. Red blood cell culture control; M. Low molecular weight standard (97, 66, 45, 30, 20.5, 14.4 kDa). The result indicated that after the antisera against the mixed polyepitope chimeric gene vaccine in the No. 3 library were 3000× diluted, they still were able to recognize the various 3D7 antigens treated with Spanin.

FIG. 10 shows cross protection by the mixed polyepitope chimeric gene vaccines from different libraries against *Plasmodium yoelii*.

In the presence of an empty vector and saline as parallel controls, the mixed polyepitope chimeric gene vaccines from different libraries (Libraries No. 2, No. 3, No. 4 and No. 5) were used to immunize Balb/c mice (seven in each group) for three times prior to the challenge with $2 \times 10^5$ infectious *Plasmodium yoelii* by peritoneal injection. The death of mice was observed in every three days. The results indicated that No. 2, No. 3 and No. 4 libraries elicited protective effect, wherein the protection rate of the polyepitope genes from No. 3 library (with a size of about 1200 bp) was up to 42.8%.

FIG. 11 shows a Western blot of the prokaryotic expression of antigen genes with high immunogenicity. FIG. 11A. SDS-PAGE; FIG. 11B. hybridization membrane. 1. positive clone SP312 selected; 2. the vector; 3. negative clone SN33; 4. SN34; 5. SP352; 6. SN36.

FIG. 12 shows the detection of cytokines involved in in vivo immune response elicited by the positive (SP) and negative (SN) clones screened from the libraries.

DETAILED DESCRIPTION OF THE INVENTION

The principle of the present invention is illustrated in FIG. 1.

According to the method of the invention, the antigen of interest is any antigen related to various infectious diseases, tumors or autoimmune diseases. Many sequences of the antigen epitopes are known in the art, and based on these sequences it is possible to synthesize a plurality of the nucleic acid molecules, each nucleic acid encoding a single epitope of an antigen of interest in step a).

After the nucleic acid molecules encoding a single epitope of an antigen of interest are cloned into vectors, these genes encoding a single epitope are randomly assembled to form bi-epitope genes according to the method of the present invention using the isocaudamer technique. Various isocaudamers are known in the art, which may be used in the method of the present invention.

According to the method of the invention, after bi-epitope genes are obtained, they need to be randomly assembled into polyepitope chimeric genes. To increase the randomicity of the tandem recombination between different epitopes, in one preferable embodiment of the present invention, two approaches are carried out simultaneously to randomly assemble polyepitope chimeric genes with different lengths:
1) combined polymerase chain reaction and primer-free polymerase chain reaction; and 2) random linking with the aid of the isocaudamer sites on the vector.

The obtained randomly assembled polyepitope chimeric genes with different lengths are separated according to the various length ranges which may be set according to the requirements and which are usually from hundreds to thousands of base pairs. In one embodiment of the invention, five groups of randomly assembled polyepitope chimeric genes of respectively 300, 800, 1200, 2000 and 4000 bp are separated. It is understood that one skilled in the art may set any desired length ranges. Then these separated groups of polyepitope chimeric genes may be cloned into any appropriate expression vector known in the art after being purified and amplified, and used to transform appropriate host cells to obtain several expression libraries of polyepitope chimeric genes.

According to the invention, after expression libraries of polyepitope chimeric genes are obtained, the diversity of the libraries and the immunogenicity of the expression products of the libraries are detected, so that one or more gene libraries comprising optimally assembled polyepitope chimeric gene vaccines are selected to further screen and prepare polyepitope chimeric gene vaccines. Preferably, the diversity of the libraries is above 85%. The criteria to determine the optimal assembly are based on the high diversity of the libraries and high immunogenicity of the expression products. In addition, the criteria may include the immunological characteristics related to the antigen epitopes of interest, such as the specific immunological types and cytokines generated in the body elicited by the libraries tested or the cross protective effects elicited in animal models.

In the examples of the invention, the inventors selected antigen epitope sequences which were proved to be high immunogenic in the literature on *Plasmodium falciparfum* (Table 1), and using human preferential codons modified the corresponding coding sequences (Table 2). Fourteen epitope fragments were repeated and then ligated randomly to construct artificial antigen libraries with different lengths wherein each library contained thousands of artificial antigens of different combination. After mice were immunized with the polyepitope gene libraries, a very high level of specific antibody was obtained in the serum. With a *Plasmodium yoelii* mouse model, it had been demonstrated that these artificial antigens were able to elicit cross-immunol protection, thereby indicating that the expression libraries constructed according to the method of the present invention overcame the drawbacks in the existing libraries and laid a foundation for ideal polyepitope chimeric gene vaccines. The primary screening result for the libraries in Example 6 indicated that polyepitope chimeric gene vaccines with higher immunogenicity may be obtained by high-throughput immunochemistry methods.

The advantages of immunization of the body with the chimeric gene expression libraries according to the invention, which differ from that with cDNA expression libraries, lie in that the polyepitope chimeric gene libraries eliminate the interference of non-epitope DNA sequences associated with the use of cDNA expression libraries (Shibui A. et al. Res Commun Mol Pathol Pharmacol, 109 (3-4), 147-57 (2001); Smooker P. M. et al. Vaccine, 18 (23), 2533-40 (2000); Johnston S. A. et al. Vaccine, 15 (8), 808-9 (1997)), and improve the safety of gene vaccines. Also one skilled in the art could select targets for gene immunization and challenge, prepare more quickly efficient gene vaccines, and recognize the genes in libraries which indeed have protective effect so as to facilitate analysis of gene function.

In the following examples, polyepitope chimeric gene vaccines against malignant malaria were prepared. These examples are intended to illustrate the invention only, not limit the scope of the invention. One skilled in the art would understand that the method of the present invention is not limited to the preparation of polyepitope chimeric gene vaccines against malignant malaria, but may be used in the preparation of gene vaccines against various infectious diseases, tumors or autoimmune diseases.

The invention is further illustrated in detail by the following figures and examples.

Example 1

Cloning and Sequence Analysis of the Functional Fragments of the Epitope Gene Fragments of *Plasmodium falciparum*

1. Modification of the DNA Sequences Encoding Epitopes of B Cells and Th Cells in Different Life Stages In order to inhibit the growth of *Plasmodium falciparfum* more effectively and test the protection in a *Plasmodium yoelii* animal model of malaria, fourteen epitopes from nine surface antigens MSP-1, RESA, MSA-2, AMA-1, EBA-175, LSA-1, CS.T3, NKND and MAg-1 found in various life stages of *Plasmodium falciparfum* which are homologous to those of *Plasmodium yoelii* were selected (Table 1) based on the published literatures, wherein the nucleotide sequences corresponding to the amino acid sequences of the epitopes were generated using human preferential codons (Table 2, the nucleotide sequences in bold).

2. Design and Synthesis of Primers for the Epitope Gene Fragments a) Based on the epitope gene sequences modified in above step 1, two primers with complete complementary 3' ends were designed (Table 2, the complementary sequences were the overlapping sequences between two primers), and isocaudamer sites of BcI/I and BamHI were introduced into the upstream and downstream primers for the epitope gene sequences, respectively.

b) A structure of Gly-Pro-Gly-Pro (G-P-G-P) (SEQ ID NO: 1) was introduced near the BclI and BamHI linkage site of the different linked antigen epitopes in order to increase the steric flexibility of the epitope linkages.

c) For longer epitope gene fragments (such as E3$_{(MSA2)}$ and E6$_{(MSA1)}$), four primers were used to obtain the full-length genes by twice annealing and extension.

3. Cloning and Sequence Analysis of the Epitope Gene Fragments a) The matched sequences between the two complementary primers were allowed to anneal and extend under the PCR conditions of 94° C., 30 sec, 45-60° C. (depending on the Tm of different primers), 30 sec, and 72° C., 40 sec, 40 cycles.

b) The amplification products were precipitated by 1/10 volume of 10M ammonium acetate and 2 volume of pure ethanol, then resolved in ultra-purified water, digested with BclI and BamHI and treated with equal volume of phenol, followed by centrifugation at 12000 rpm for 5 mm. The supernatant was precipitated by 1/10 volume of 3M sodium acetate and 2 volume of pure ethanol, and then resolved in ultra purified water.

c) The digested product was ligated to vector VR1012 (Vical Inc.) which had been digested with same enzymes, and then transformed into *E. coli* strain SK383 (deficient in GATC methylation). The target clones were selected by Bc/I and BamHI cleavage.

d) The target clones were sequenced with primer C038P which has a sequence of 5'-CCAGACATAATAGCTGAC-3' and which is a sequence upstream the multiple cloning sites of vector VR1012.

Example 2

Random Assembly of Epitope Genes of *Plasmodium falciparfum*

1. Construction of Randomly Assembled Bi-Epitope Genes

To generate matched regions among epitope genes which have very low homology, the individual single epitope genes cloned in step 3 of Example 1 were ligated to form bi-epitope genes by using isocaudamer sites of Bc/I and BamHI in conjunction with a Hind/III site. Briefly, for the randomization of ligation and improvement of efficiency, various single genes were mixed in equal amounts and divided into two aliquots. One was cleaved with Bc/I and Hind/III, the other with BamHI and Hind/III. And the fragments from the two digestions which contain epitope genes were mixed and ligated, then electrotransformed into *E. coli* strain SK383 to obtain clones containing randomly assembled bi-epitope genes.

2. Construction of Randomly Assembled Polyepitope Genes of Different Lengths

In order to increase the randomicity of the recombination of different epitopes, two protocols, polymerase chain reaction and random linkage by isocaudamers, were used to construct the randomly assembled polyepitope genes, and finally the products from these two protocols were mixed to construct five polyepitope gene libraries (FIG. 4) with different lengths (about 300, 800, 1200, 2000 and 4000 bp, respectively).

a) Construction by Polymerase Chain Reaction

The bi-epitope recombinant plasmids in above step 1 were mixed, subsequently cleaved with Bc/I and BamHI, and subjected to electrophoresis on a low melting point agarose gel. The small fragments were retrieved with DNA purification kits (Promega), and measured at $OD_{260}/OD_{280}$ for their concentrations.

A reaction system for primer-free polymerase chain reaction (50 µl) was prepared with the following components:

| Mixed bi-epitope DNAs | 1 µl |
| ExTaq DNA polymerase (5 U/µl) | 2 U |
| 10X buffer | 5 µl |
| dNTP | 8 µl |
| d$_2$H$_2$O | 36 µl |

The reaction conditions (25, 35, 45, 55, 65, 75, or 85 cycles) were as follows. First procedure, 94° C., 3 min; 94° C., 30 sec; 42-55° C., 30 sec; 72° C., 30 sec; 25 cycles; and 72° C., 10 min. Second procedure: 94° C., 3 min; 94° C., 45 sec; 50-55° C., 45 sec; 72° C., 30 sec, 1 sec/cycle; 10 cycles; and 72° C., 10 min. The products of the primer-free amplification were subjected to 1% agarose gel electrophoresis and the results were shown in FIG. 2, which showed that the assembled polyepitope gene fragments had increased length with the increase of the cycle number. Five DNA fragments with different lengths (about 300, 800, 1200, 2000 and 4000 bp, respectively) were retrieved from the gel and subjected to a conventional PCR reaction with upstream primer 5'-ACAT-CATGCCTGATCA-3' and downstream primer 5'-TTAGCTAGCGGATCC-3'. The reaction system was the same as that for the primer-free PCR, with a procedure: 94° C., 3 mm; 94° C., 30 sec; 50° C., 30 sec; 72° C., 30 sec; 30 cycles; and 72° C. 10 min. The amplification products were purified and concentrated by wizard PCR prep purification kit (Promega), then cleaved with Bc/I and ligated into vector VR1O12 which had been cleaved with EcoRV and Bc/I, and the ligation mixture were electrotransformed into *E. coli* strain SK383. The methods and results were set forth in FIG. 1 and FIG. 2.

b) Random Linkage by Isocaudamers

The bi-epitope recombinant plasmids in above step 1 were mixed. Small fragments cleaved with Bc/I/BamHI (containing epitope genes) were ligated with large fragments cleaved with BamHI/HindIII (containing epitope genes), and then the ligation mixture was electrotransformed into competent cells SK383 to form random assembled tetra-epitope libraries. Similarly, five random libraries of polyepitope genes with different lengths (about 300, 800, 1200, 2000 and 4000 bp, respectively) were constructed.

Example 3

Construction of Expression Libraries of Polyepitope Chimeric Genes of *Plasmodium falciparfum*

1. Construction of Eukaryotic Expression Vectors VR10A and VR10T Containing Kozak Sequence and Termination Codon, Respectively.

Primers (1A: 5'-GATCACCATGGAATTCG-3' (SEQ. ID. No. 16) and 1B: 5'-GATCCGAATTCCATGGT-3' (SEQ ID No. 17)) containing eukaryotic Kozak sequence were designed and then were allowed to self anneal and extend. The PCR product was cleaved with bc/I and BamHI and cloned into vector VR1012 with *E. coli* strain SK383 as the recipient strain, thereby a recombinant plasmid VR10A was obtained and sequenced by Takara Biotech Company.

In order to facilitate the subsequent functional analysis of polyepitope genes after the random construction, the termination codon TAATAA was placed downstream of the epitope $E6_{(MSA-1)}$ (Table 2, primer 6D for gene E6). Primers 6A, 6B, 6C and 6D were synthesized, and allowed to self anneal and extend. The PCR product was cleaved with Bc/I and Bg/II and cloned into vector VR012 with *E. coli* strain SK383 as the recipient strain, thereby a recombinant plasmid VR10T was obtained and sequenced by Takara Biotech Company.

2. Construction of Five Expression Libraries of Polyepitope Genes with Different Lengths a) Plasmid DNAs from the five polyepitope gene libraries with different lengths prepared in step 2 of Example 2 were cleaved with Bc/I and HindIII. The obtained fragments (containing epitope genes) were retrieved and respectively ligated with plasmid VR10A cleaved with BamHI and HindIII (containing start codon), then electrotransformed into competent cells SK383 to obtain recombinant plasmids.

b) Similarly, five recombinant plasmids in step a) were cleaved with Bc/I/HindIII and BamHI/HindIII and ligated with the DNA fragment of vector VR10T in above step 1 containing the termination codon to construct five expression libraries (No. 1, No. 2, No. 3, No. 4 and No. 5, respectively) of polyepitope genes with different lengths (about 300, 800, 1200, 2000 and 4000 bp, respectively), as shown in FIG. 4.

3. Analysis of Gene Diversity of the Expression Libraries of Polyepitope Chimeric Genes Libraries No. 3 and No. 4 were tested for the single-strand conformational pleiomorphism (PCR-SSCP). The results indicated that the diversity in the chimeric genes of both libraries was higher than 95% (24/25 and 25/25, respectively), as shown in FIG. 5. The steps for this test were as follows:

a) 25 clones were selected randomly from the libraries and PCR was carried out with primer (C038P: 5'-CCAGACATAATAGCTGAC-3') upstream of multiple cloning sites of vector VR1012 and primer (C039P: 5'-GATGGCTGGCAACTAGAA-3') downstream of multiple cloning sites of vector VR1012 (amplification conditions: 94° C., 30 sec; 55° C., 30 sec, 72° C., 1 min, 30 cycles). The amplification products were incubated in boiling water bath for 10 min and chilled on ice for 10 min, then mixed with 10× sample buffer.

b) The above samples were subjected to 10% polyacrylamide gel and ran at 5 V/cm. After electrophoresis, the gel was firmly on the glass.

c) The glass with gel was put into a Petri dish and fixing buffer (10% glacial acetic acid v/v) was added to submerge the gel for at least 20 mm with horizontally shaking slowly. After fixation, the fixing buffer was collected and used as fixer after development.

d) The gel was rinsed with double distilled water three times.

e) A staining solution (2 g $AgNO_3$, 3 ml 37% formaldehyde in 2 liters of deionized water) was added and the dish was slowly shaken for 30 min.

f) The gel was rinsed with double distilled water for 20 sec (note: the rinse time should not be too long).

g) A precooled developing solution (60 g $Na_2CO_3$, 3 ml 37% formaldehyde, 400 μl 10 mg/ml sodium thiosulfate were added in 2 liters of deionized water, and placed in water bath until the temperature was 10-12° C.) was added and the dish was slowly shaken until the bands were visualized in gel (usually 5-6 min).

h) An equal volume of fixing solution was added into the dish to stop the developing reaction, and the dish was slowly shaken for 2-3 min.

i) The gel was rinsed with double distilled water three times.

j) The gel was air-dried and detected under lamp.

Example 4

Detection of the Immunogenicity of the Five Polyepitope Gene Libraries

1. Preparation of Recombinant Plasmids Containing the Polyepitope Genes of Different Libraries Bacteria containing the polyepitope gene libraries with different lengths (No. 1, No. 2, No. 3, No. 4 and No. 5) constructed in step 2 of Example 3 were washed respectively from the plates, and cultured in LB liquid medium with corresponding antibiotics. Then an inoculum was used to inoculate 1 liter of LB liquid medium with corresponding antibiotics at a ratio of 1:100, and the bacteria were cultured to logarithmic growth phase. The bacteria were collected. Plasmids were extracted according to Wizard Megapreps plasmid extraction kit (Promega). DNA concentration was calculated from $OD_{250}/OD_{280}$ measured with DU7O ultraviolet spectrophotomer (Beckman).

2. Preparation of Antisera of Mice Immunized with the Polyepitope Chimeric Gene Libraries 100 μg DNAs of the recombinant plasmids of the gene vaccine libraries 30 obtained in above step 1 were adjusted to equal volume with sterile saline. Groups of Balb/c mice were immunized by injecting equal volume of such DNAs into humerus quadriceps of both legs, with three animals in each group. The empty vector and blank without DNA were taken as controls. Immunization was boosted every two weeks, totally three times. Blood samples were taken from each group and the polyclonal antisera were collected after immunization.

3. Detection of Antibody Levels Generated by Different Polyepitope Gene Libraries by Enzyme Linked Immunosorbent Assay (ELISA)

In the presence of positive control, negative control and blank control, mixed epitope synthetic peptides were used as coating antigens. The antisera to be tested were two-fold diluted (such as 400, 800, 1600, 3200, 6400, 12800, 25600 and 51200). The maximal dilution (titre) of the antisera after immunization with different polyepitope gene libraries were detected by ELISA, as shown in FIG. 6. The results indicated that the gene libraries with different lengths had different immunogenicity and high titers of antibodies were generated. The specific steps for the assay were as follows:

a) Coating: synthetic peptides of a single or mixed epitopes were used as coating antigens, and diluted with a coating buffer of 0.1 M carbonate, pH 9.2 into a desired concentration (200 ng/100 μl/well). 100 μl was added into each well by a pipette and then the plate was placed in humidified environment overnight at 4° C. or for 4 h at 37° C. The plate was decanted and rinsed with PBST five times.

b) Blocking: 200 μl of 1% BSA was added into each well, and the plate was incubated at 37° C. for 1 h.

c) The plate was rinsed with PBST five times.

d) Addition of antisera derived from mice to be tested: the antisera to be tested were two-fold diluted with PBS solution, and 100 μl of the diluted antisera with each concentration in triplicate was added into each well and incubated overnight at 4° C.

e) The plate was rinsed with PBST five times.

f) Addition of an antibody labeled with horseradish peroxidase, i.e. horse-anti-mouse IgG-HRP: 100 μl of the labeled antibody diluted with PBS/BSA (1:1000) was added into each well and incubated for 2 h at 37° C. in humidified environment.

g) The plate was rinsed with PBST five times.

h) Development: 100 μl of a substrate developing buffer was added into each well and the plate was placed at room temperature for 10 min.

i) 50 μl of 1 M $H_2SO_4$ was added into each well to stop reaction.

j) The absorbance at 450 nm was read with Labsystems Genesis V3.03 system and the result was analyzed.

Substrate developing buffer (pH5.0)

Solution A: 1.92 g of citrate (anhydrous) was added into dd$H_2$O with a final volume of 100 ml.

Solution B: 7.16 g of $Na_2HPO_4$ (containing 12 water of crystallization) was added into dd$H_2$O with a final volume of 100 ml.

2.43 ml of Solution A, 2.57 ml of Solution B and 5 ml of water were mixed to form 10 ml of phosphate-citrate buffer, pH5.0.

Prior to developing reaction, 0.015 ml of 30% Hydrogen peroxide and 0.004 g of TMB were added into the 10 ml of phosphate-citrate buffer to freshly prepare the developing buffer.

4. Detection results of indirect immunofluorescence assay (IFA) for the recognition of native proteins by the polyclonal antisera generated by the different polyepitope gene libraries.

In order to determine whether or not the antisera generated by the different polyepitope gene libraries recognize native proteins of *Plasmodium falciparum* and *Plasmodium yoelii*, an indirect immunofluorescence assay (IEA) was used. In the presence of a positive control, the maximum dilution of antibody which permits the recognition was determined and confocal microscopy was used to determine the binding sites of antibody, the results were shown in FIGS. 7 and 8. The specific steps of this assay were as follows:

1) Recognition of Native Proteins of *Plasmodium falciparfum* a) Blood cells with erythrocytic stage *Plasmodium falciparfum* 3D7(or FCC1) (with an infection rate of about 2%) were uniformly spread on slides and the slides were air-dried at room temperature.

b) 100% acetone was used to fix the cells for 10 min.

c) The slides were air-dried at room temperature and marked with a fluorescent marker pen, and 1% BSA in PBS was added to block for 30 min at room temperature.

d) The slides were rinsed with PBS three times, each for 10 min, and air-dried.

e) Different dilutions (1:500, 1:1000, 1:2000, 1:4000) of the primary antisera (the antisera from the mice as above) were added, and the slides were incubated at room temperature for 30 min in humidified environment. MAb M26-32 was taken as a positive control.

f) The slides were rinsed with PBS three times, each for 10 min, and air-dried.

g) A horse-anti-mouse IgG labeled with FITC diluted by 1:100 was added, and the slides were incubated at 37° C. for 30 min in humidified environment.

h) The slides were rinsed with PBS three times, each for 10 min, and air-dried.

i) A coverslip was sealed on the slide by 50% glycerol and fluorescent microscopy or confocal fluorescence microscopy were used to visualize.

2) Cross-Recognition of native proteins of *Plasmodium yoelii* a) Blood cells with *Plasmodium yoelii* (with an infection rate of about 50%) was uniformly spread on slides and the slides were air-dried at room temperature.

b) other steps were same as those for the recognition of native proteins of *Plasmodium falciparfum* in above section 1).

5. Western Blot Detection of Antisera Generated by the Various Polyepitope Gene Libraries In order to show the recognition of the native antigens of *Plasmodium falciparfum* by the antisera generated by the various polyepitope gene libraries, antisera obtained in step 2 of Example 4 were diluted, and subjected to Western blot with the parasite proteins which had been isolated by SDS-PAGE from the Spanin-treated *Plasmodium falciparfum*. Polyepitope library No. 3 was used in the experiment, and the result indicated that the antisera generated by the gene vaccines in library No. 3 recognized more than ten parasite proteins with different sizes, and had high level of antibodies. The result was shown in FIG. 9. The specific steps for this experiment were as follow:

a) Treatment of the sample: the culture of one or two dishes of *Plasmodium falciparfum* strain 3D7 was collected by centrifugation, washed with PBS twice, and treated with Spanin at a final concentration of 0.2% to rupture red blood cells. Then the pellet was washed with PBS twice, resolved in PBS, mixed with 10× sample buffer and incubated in a boiling water bath for 10 min.

b) Immunoblotting: the treated sample was subjected to SDS-PAGE electrophoresis for separation. After electrophoresis, proteins were electrotransferred onto a nitrocellulose membrane, and then the membrane was blocked by 3% BSA at room temperature for 1 h, and rinsed with PBS three times. A given amount of the antiserum generated by the gene library diluted with BSA was added and the membrane was incubated at room temperature for 1 h. After the membrane was washed with PBS three times, a secondary antibody horse-anti-mouse IgG (Ap-IgG) labeled with alkaline phosphatase was added and incubated at room temperature for 1 h. The membrane was washed with PBS three times. Finally the membrane was rinsed with an alkaline phosphatase buffer (100 mmol/L Tris-HCl (pH9.5), 100 mmol/L NaCl, 5 mmol/L MgCl$_2$) once.

c) Development and stopping the development: 33 μl of nitroblue tetrazolium (50 mg/ml in 70% dimethylsulfoxide) and 16.5 μl of 5-bromo-4-chloro-3-indo-lyl-phosphate solution (10 mg/ml in 100% dimethylsulfoxide) were added per 5 ml of alkaline phosphatase buffer. After 10 min, a stop buffer (20 mmol/L Tris-HCl (pH8), 5 mmol/L EDTA) was added to stop the reaction.

Example 5

Cross-Protection Against *P. yoelii* by Polyepitope Chimeric Gene Vaccines from Different Libraries In order to construct polyepitope chimeric gene vaccines against malignant malaria more efficiently, we tested the protection role of the gene vaccines of the invention in a *P. yoelli* animal model. The result indicated that the five polyepitope gene libraries all exhibited protection with varying extent (FIG. 10), which laid a foundation for an in vivo protection model related to the protection role of the artificial shuffled gene vaccines against *Plasmodium falciparum*. The specific steps of the experiment were as follow:

a) A sample of *P. yoelii* was removed from liquid nitrogen and thawed at 37° C. water bath. 500 μl of the sample was injected into Balb/c mice peritoneally. Several days later, a blood sample was taken and spread on a slide, fixed by methanol, and stained with Giemsa and infection rate was counted under a microscope.

b) The blood of mice infected with *P. yoelii* was collected from the tails and dropped into CPBS buffer (NaCl 3.2 g, KCl 0.08 g, Na$_2$HPO$_4$.12H$_2$O 1.16 g, KHPO$_4$ 0.08 g, Na-citrate 3.8 g, adding water to 500 ml, pH7.2). The concentration of the red blood cells infected by the parasite was calculated by a haemacytometer.

c) Balb/c mice immunized in step 2 of Example 4 were injected peritoneally with the blood obtained as above at a dose of 2×10$^5$ red blood cells infected/mouse.

d) Every three days, antisera were collected from the tails of the mice and spread on slides to calculate the infection rate. Also the survival rates of the control and experiment groups were observed.

Example 6

In Vivo Test of the Polyepitope Chimeric Gene Vaccines with High Immunogenicity Obtained by High-Throughput Immunochemistry Method According to the results from the in vivo immunogenicity test of the polyepitope gene libraries (Example 4) and the test of the protection against *P. yoelii* challenge (Example 5), the polyepitope gene libraries with high level of immunologic response and protection were selected. According to the screening protocol of high-throughput immunochemistry, several positive clones with high immunogenicity were obtained. In the presence of the negative gene clones and empty vectors randomly selected, Western blot detection was carried out for the prokaryotic expression, and cytokines CD4 and CD8 involved in the immunologic response in mice were examined.

1. Western Blot Detection for the Prokaryotic Expression

The result indicated that high immunogenic genes SP312 and SP352 obtained by screening expressed corresponding proteins. After the antibodies generated by use of these two genes were highly diluted, positive hybridization band was still found by Western blot detection, while no signal band was observed when using low immunogenic genes SN33, SN34, and SN36 and empty vector negative control, indicating that polyepitope genes SP312 and SP352 generated higher titre of antibody than genes SN33, SN34 and SN36 (FIG. 11).

2. Detection of Cytokines CD4 and CD8 Involved in the Immunologic Response in Mice The obtained positive (high immunogenic) gene clones SP3I2. SP352 and SP462 were confirmed by in vivo immunization. In the presence of negative (low immunogenic) gene clones and empty vector, Balb/c mice were immunized three times, and spleen lymphocytes were isolated for the s detection of cytokines CD4 and CD8 using flow cytometry. The results indicated that positive (high immunogenic) gene clones SP312, SP352 and SP462 predominantly induced the production of cytokine CD4, accompanied with certain level of cytokine CD8, wherein positive polyepitope gene 5P312 generated a level of cytokines markedly higher than that of 5P352 or SP462. In contrast, negative polyepitope genes behaved similar to empty vector, demonstrating that polyepitope chimeric gene vaccines with higher immunogenicity can be obtained by high-throughput immunochemistry method (FIG. 12).

TABLE 1

Amino acid sequences of B- and Th- cell epitopes of antigens of *Plasmodium falciparum* in different life stages used in the invention

| Epitope gene | Amino acids sequence | Seq. ID | Antigen gene | Life stage | Types of immunocyte | Reference |
|---|---|---|---|---|---|---|
| E2 (NKND) | NKNDNKND | Seq ID No: 2 | NKND | Cross | B | Cheng Q, 1991 |
| E3 (MSA-2) | KNESKYSNTFINNAYNMSIRRSM | Seq ID No: 3 | MSA-2 | Erythrocytic stage | B/Th | Symthe J A, 1991 |
| E4 (RESA) | EENVEHDA | Seq ID No: 4 | RESA | Erythrocytic stage | B | Chauhan V S, 1993 |
| E5 (EBA-175) | EREDERTLTKEYEDIVLK | Seq ID No: 5 | EBA-175 | Erythrocytic stage | B | Sim B K, 1994; 1998 |
| E6 (MSA-1) | LDNIKDNVGKMEDYIKKNKK | Seq ID No: 6 | MSA-1 | Erythrocytic stage/liver stage | B/Th | Kumar A, 1992; Chauhan Y S, 1993 |
| E7 (LSA-1) | EQQSDLEQERL(R)AKEKLQ | Seq ID No: 7 | LSA-1 | liver stage | B/Th | Aidoo M, 2000 |
| E8 (CS.T3/CSP) | KKIAKMEKASSVFNV | Seq ID No: 8 | CS.T3/CSP | sporozoite stage | Tb | Sinigaglia F, 1988 |

TABLE 1-continued

Amino acid sequences of B- and Th- cell epitopes of antigens of
*Plasmodium falciparum* in different life stages used in the invention

| Epitope gene | Amino acids sequence | Seq. ID | Antigen gene | Life stage | Types of immunocyte | Reference |
|---|---|---|---|---|---|---|
| E9 (MSP-1) | NSGCFRHLDEREECKCLL | Seq ID No: 9 | MSP-1 | Erythrocytic stage | B | Chang S P, 1992 |
| E10 (MSP-1) | EDSGSNGKKITCECTKPDS | Seq ID No: 10 | MSP-1 | Erythrocytic stage | B | Chang S P, 1992 |
| E11 (AMA-1) | DGNCEDIPIIVNEFSAIDL | Seq ID No: 11 | AMA-1 | Erythrocytic stage | B | Shi Y P, 1999 |
| E12 (AMA-1) | GNAEKYDKMDEPQHYGKS | Seq ID No: 12 | AMA-1 | Erythrocytic stage | B | Lal A A, 1996 |
| E15 (AMA-1) | DQPKQYEQHLTDYEKIKEG | Seq ID No: 13 | AMA-1 | Erythrocytic stage | Th | Lal A A, 1996 |
| E16 (MSP-1) | GISYYEKVLAKYKDDLE | Seq ID No: 14 | MSP-1 | Erythrocytic stage | Th | Udhayakumar V, 1995 |
| E17 (MAg-1) | QTDEIKNDNI | Seq ID No: 15 | MAg-1 | Erythrocytic stage | B/Th | Lu Y, unpublished |

TABLE 2

Primer sequences for cloning epitope genes

| Epitope genes | Seq ID | Primer sequence |
|---|---|---|
| E2 (NKND) A | Seq ID No: 18 | 2A: 5'-ACATCATGCC<u>T'CATCA</u>AACAAGAACGACAACA-3'<br>　　　　　　　　　BclI |
| B | Seq ID No: 19 | 2B: 3'-TGTTCTTGCTGTTGTTCTTGCT<u>GCCTAG'</u>GCGC-5'<br>　　　　　　　　　　　　　　　　　BamHI |
| E3 (MSA-2) A　　C | Seq ID No: 20 | 3A: 5'-ACATCATGCC<u>T'GATCA</u>AAGAACGAGAGCAAGTACAG-3'<br>　　　　　　　　　BclI |
| 　　　　 | Seq ID No: 21 | 3B: 3'-GCTCTCGTTCATGTCGTTGTGGAAGTAGTTGTTGCGGATG-5' |
| B　　D | Seq ID No: 22 | 3C: 5'-CATCAACAACGCCTACAACATGAGCATCCGCCGCAGCATGG-3' |
| | Seq ID No: 23 | 3D: 3'-GGCGGCGTCGTACCCGGGGCCGGGG<u>CCTAG'</u>GCGC-5'<br>　　　　　　　　　　　　　　　　　　BamHI |
| E4 (RESA) A | Seq ID No: 24 | 4A: 5'-ACATCATGCC<u>T'GATCA</u>GAGGAGAACGTGGAGC-3'<br>　　　　　　　　　BclI |
| B | Seq ID No: 25 | 4B: 3'-TCCTCTTGCACCTCGTGCTGCGG<u>CCTAG'</u>GCGC-5'<br>　　　　　　　　　　　　　　　BamHI |
| E5 (EBA-175) A | Seq ID No: 26 | 5A: 5'-ACATCATGCC<u>T'GATCA</u>GAGCGCGAGGACGAGCGCACCCTGACCAAGGAGTACG-3'<br>　　　　　　　　　BclI |
| B | Seq ID No: 27 | 53: 5B'-GACTGGTTCCTCATGCTCCTGTAGCACGACTTCCCGGGGCCGGGG<u>CCTAG'</u>GCGC 5'<br>　　　　　　　　　　　　　　　　　　　　　　　　　　　BamHI |
| E6 (MSA-1) A　　C | Seq ID No: 28 | 6A: 5'-ACATCATGCC<u>T'GATCA</u>CTGGACAACATCAAGGACAACGTGGGC-3'<br>　　　　　　　　　BclI |
| | Seq ID No: 29 | 6B: 3'-TCCTGTTGCACCCGTTCTACCTCCTGATGTAGTTCTTCTTGT-5' |
| B　　D | Seq ID No: 30 | 6C: 5'-TACATCAAGAAGAACAAGA.AGGGCCCCGCC'CCGGATCCG-3' |
| | Seq ID No: 31 | 6D: 3'-CGGGG<u>CCTAG'</u>GCGATCGATTATTTCTAGAAGG-5'<br>　　　　　BamHI |
| E6 (MSA-1) A | Seq ID No: 32 | 7A: 5'-ACATCATCGC<u>T'GATCAGA</u>GCAGCAGAGCGACCTGGAGCAGGAGCGCCTGG-3'<br>　　　　　　　　　BclI |
| B | Seq ID No: 33 | 7B: 3'-GTCCTCGCGGACCGGTTCCTCTTCGACGTCCCGGGGCCGGGG<u>CCTAG'</u>GCGC-5'<br>　　　　　　　　　　　　　　　　　　　　　　　BamHI |
| E8 (CS.T3/CSP) A | Seq ID No: 34 | 8A: 5'-ACATCATGCC<u>T'GATCA</u>AAGAAGATCGCCAAGATGGAGAAGGCCAGCAGC-3'<br>　　　　　　　　　BclI |
| B | Seq ID No: 35 | 8B: 3'-CTCTTCCGGTCGTCGCACAAGTTGCACCCGGGGCCGGGG<u>CCTAG'</u>GCGC-5'<br>　　　　　　　　　　　　　　　　　　　　BamHI |
| E9 (MSP-1) A | Seq ID No: 36 | 9A: 5'-ACATCATGCC<u>T'GATCA</u>AACAGCGGCTGCTTCCGCCACCTGGACGAGCCGC-3'<br>　　　　　　　　　BclI |
| B | Seq ID No: 37 | 9B: 3'-TGGACCTGCTCGCGCTCCTCACGTTCACGGACGA<u>CCTAG'</u>GCGC-5'<br>　　　　　　　　　　　　　　　　　　　BamHI |
| E10 (MSP-1) A | Seq ID No: 38 | 10A: 5'-ACATCATGCC<u>T'GATCA</u>GAGGACAGCGGCAGCAACGGCAAGAAGATCACCTGC-3'<br>　　　　　　　　　　BclI |
| B | Seq ID No: 39 | 10B: 3'-GTTCTTCTAGTGGACGCTCACGTGGTTCGGCCTGTC<u>GCCTAG'</u>GCGC-5<br>　　　　　　　　　　　　　　　　　　　BamHI |
| E11 (AMA-1) A | Seq ID No: 40 | 11A: 5'-ACATCATGCC<u>T'GATCA</u>GACGGCAACTGCGAGGACATCCCGCACGTGAAC-3'<br>　　　　　　　　　　BclI |
| B | Seq ID No: 41 | 11B: 3'-TAGGGCGTGCACTTGCTCAAGTCGCGGTAGCTGGAC<u>CCTAG'</u>GCGC-5<br>　　　　　　　　　　　　　　　　　　　BamHI |
| E12 (AMA-1) A | Seq ID No: 42 | 12A: 5'-ACATCATGCC<u>T'GATCA</u>GGCAACGCCGAGAAGTACGACAAGATGGACGAGCCG-3'<br>　　　　　　　　　　BclI |
| B | Seq ID No: 43 | 12B: 3'-TTCTACCTGCTCGGCGTCGTGATGCCGTTCTCG<u>CCTAG'</u>GCGC-5'<br>　　　　　　　　　　　　　　　　　BamHI |

TABLE 2-continued

Primer sequences for cloning epitope genes

| Epitope genes | Seq ID | Primer sequence |
|---|---|---|
| E15 (AMA-1) A | Seq ID No: 44 | 15A: 5'-ACATCATGCCT'GATCAGACCAGCCGAAGCAGTACGAGCAGCACCTGACCGAC-3'<br>　　　　　　　　　BclI |
| B | Seq ID No: 45 | 15B: 3'-GTCGTGGACTGGCTGATGCTCTTCTAGTTCCTCCCGCCTAG'GCGC-5'<br>　　　　　　　　　　　　　　　　　　　　　　　　BamHI |
| E16 (MSP-1) A | Seq ID No: 46 | 16A: 5'-ACATCATGCCT'GATCAGGCATCAGCTACTACGAGAAGGTGCTGGCCAAG-3'<br>　　　　　　　　　BclI |
| B | Seq ID No: 47 | 16B: 3'-TTCCACGACCGGTTCATGTTCCTGCTGGACCTCCCTAG'GCGC-5'<br>　　　　　　　　　　　　　　　　　　　　　BamHI |
| E17 (MAg-1) A | Seq ID No: 48 | 17A: 5'-ACATCATGCC<br>T'GATCACAGACCGACGAGATCAAGAACGACCACATCCAGACCGAT-3'<br>　　　BclI |
| B | Seq ID No: 49 | 17B: 3'-GTGTAGGTCTGGCTACTTTAATTTTTACTATTATAACCTAG'GCGC-5<br>　　　　　　　　　　　　　　　　　　　　　　　BamHI |

We claim:

1. A method for preparing polyepitope chimeric gene vaccines, the method comprising the steps of:
   a) selecting, synthesizing, and cloning Into a vector a plurality of nucleic acid molecules each encoding a single epitope of an antigen of interest;
   b) constructing nucleic acid molecules encoding randomly combined bi-epitopes in the vectors of step a) by isocaudamer linkage;
   c) randomly assembling the nucleic acid molecules encoding bi-epitopes into polyepitope chimeric genes with different lengths;
   d) (i) isolating the polyepitope chimeric genes with different lengths into a plurality of different length ranges,
      (ii) purifying and amplifying the isolated polyepitope chimeric genes,
      (iii) subcloning the isolated polyepitope chimeric genes into expression vectors to obtain polyepitope chimeric gene expression libraries,
   e) assessing the diversity of the polyepitope chimeric genes in the polyepitope chimeric gene expression libraries;
   f) (i) immunizing animals with the polyepitope chimeric gene expression libraries to provide expression products of the genes;
      (ii) detecting the immunogenicity of the expression products of the genes;
   g) selecting at least one polyepitope chimeric gene expression library based on the diversity of the polyepitope gene expression libraries and the immunogenicity of the expression products of the genes in the polyepitope gene expression libraries; and
   h) screening the selected at least one polyepitope chimeric gene expression library to identify polyepitope chimeric gene clones for use as polyepitope chimeric gene vaccines.

2. A method according to claim 1 wherein the at least one polyepitope chimeric gene expression library is screened by at least one high-throughput immunochemistry method.

3. A method according to claim 1 wherein the expression libraries selected have high diversity as measured by single strand conformation polymorphism.

4. A method according to claim 1 wherein the expression libraries selected have polyepitope chimeric genes having a diversity of greater than 85%.

5. A method according to claim 1 wherein the expression products of the genes in the selected gene libraries have high immunogenicity.

6. A method according to claim 5 wherein the immunogenicity is determined in terms of antiserum titer.

7. A method according to claim 1 wherein the expression libraries selected have immunological characteristics related to a predetermined antigen epitope.

8. A method according to claim 7 wherein the predetermined antigen epitope elicits the generation of a specific cytokine.

9. A method according to claim 7 wherein the predetermined antigen epitope elicits a cross-protective effect in an animal model.

10. A method for preparing polyepitope chimeric gene vaccines, comprising the steps of:
   a) selecting, synthesizing and cloning Into a vector a plurality of nucleic acid molecules each encoding a single epitope of an antigen of interest;
   b) constructing nucleic acid molecules encoding randomly combined bi-epitopes in the vectors of step a) by isocaudamer linkage;
   c) randomly assembling the nucleic acid molecules encoding bi-epitopes of step b) into polyepitope chimeric genes with different lengths;
   d) (i) isolating the polyepitope chimeric genes into a plurality of different length ranges, (ii) cloning the polyepitope chimeric genes into expression vectors to obtain polyepitope chimeric gene expression libraries, the expression libraries corresponding to the different length ranges into which the polyepitope chimeric genes were isolated;

e) assessing the diversity of the polyepitope chimeric genes in the polyepitope chimeric gene expression libraries and selecting at least one polyepitope chimeric gene library based on diversity for use in preparing polyepitope chimeric gene vaccines.

11. The method of claim 10 further comprising (i) immunizing animals with the polyepitope chimeric gene expression libraries to provide expression products of the genes, and (ii) detecting the immunogenicity of the expression products of the genes.

12. The method of claim 10 further comprising screening the selected at least one polyepitope chimeric gene expression library to identify polyepitope chimeric gene clones for use as polyepitope chimeric gene vaccines.

13. The method according to claim 1, wherein the randomly assembling of the polyepitope chimeric genes with different lengths in step c) is carried out simultaneously by following two methods: combined polymerase chain reaction and primer-free polymerase chain reaction, and isocaudamer linkage in the vector for random assembling.

14. The method according to claim 1, wherein the antigen of interest in step a) is an antigen related to infectious diseases, tumors or autoimmune diseases.

15. The method according to claim 14, wherein the antigen of interest in step a) is an antigen of *Plasmodium falciparum*.

16. The method according to claim 10, wherein the randomly assembling of the polyepitope chimeric genes with different lengths in step c) is carried out simultaneously by following two methods: combined polymerase chain reaction and primer-free polymerase chain reaction, and isocaudamer linkage in the vector for random assembling.

17. The method according to claim 10, wherein the antigen of interest In step a) is an antigen related to infectious diseases, tumors or autoimmune diseases.

18. The method according to claim 17, wherein the antigen of interest in step a) is an antigen of *Plasmodium falciparum*.

* * * * *

UNITED STATES PATENT AND TRADEMARK OFFICE
CERTIFICATE OF CORRECTION

| | | |
|---|---|---|
| PATENT NO. | : 7,981,601 B2 | |
| APPLICATION NO. | : 10/566697 | |
| DATED | : July 19, 2011 | |
| INVENTOR(S) | : Heng Wang and Qiliang Cai | |

It is certified that error appears in the above-identified patent and that said Letters Patent is hereby corrected as shown below:

Coversheet, FOREIGN PATENT DOCUMENTS
Foreign Patent Document reads "EP    0198328    A1    10/1986"
             should read -- EP    0198328    A2    10/1986 --

Abstract, line 8, reads "tion results in the induction of high level of specific antibodies"
        should read -- tion results in the induction of a high level of specific antibodies --

Column 1, line 44, reads "Ther, 3 (1), 31-36 (2001)), there is no related literature or"
        should read -- Ther, 3 (1), 31-36 (2001)), there are no related publications or --

Column 1, line 66, reads "therapy of allergic response and tolerance in new born infants."
        should read -- therapy of allergic response and tolerance in newborn infants. --

Column 2, line 13, reads "binant vaccines. Moreover, it is problem that the synthesis of"
        should read -- binant vaccines. Moreover, it is a problem that the synthesis of --

Column 2, line 60, reads "vaccines are directed can not generate satisfactory protective"
        should read -- vaccines are directed cannot generate satisfactory protective --

Column 3, line 35, reads "according to the results of step e) and f);"
        should read -- according to the results of steps e) and f); --

Column 3, line 42, reads "a) selecting, synthesizing and cloning into a vector a plu-"
        should read -- a) selecting, synthesizing and cloning into a vector plu- --

Column 4, line 16, reads "ture of random assembled bi-epitope genes as templates (in"
        should read -- ture of randomly assembled bi-epitope genes as templates (in --

Signed and Sealed this
Twentieth Day of December, 2011

David J. Kappos
*Director of the United States Patent and Trademark Office*

CERTIFICATE OF CORRECTION (continued)

U.S. Pat. No. 7,981,601 B2

Column 4, line 18, reads "respectively), and in a 50 ul system primer free polymerase"
    should read -- respectively), and in a 50 ul system a primer-free polymerase --

Column 5, line 4, reads "A. A blood smear of Plasmodium falciparfum 3D7; B. A"
    should read -- A. A blood smear of Plasmodium falciparum 3D7; B. A --

Column 5, line 5, reads "blood smear of Plasmodium falciparfum FCC1; C. A blood"
    should read -- blood smear of Plasmodium falciparum FCC1; C. A blood --

Column 6, line 31, reads "immunogenic in the literature on Plasmodium falciparfum"
    should read -- immunogenic in the literature on Plasmodium falciparum --

Column 6, line 52, reads "which differ from that with cDNA expression libraries, lie in"
    should read -- which differ from that with cDNA expression libraries, lie in the fact --

Column 7, line 18, reads "In order to inhibit the growth of Plasmodium falciparfum"
    should read -- In order to inhibit the growth of Plasmodium falciparum --

Column 7, line 23, reads "stages of Plasmodium falciparfum which are homologous to"
    should read -- stages of Plasmodium falciparum which are homologous to --

Column 7, line 35, reads "damer sites of Bc1/I and BamHI were introduced into the"
    should read -- damer sites of Bc/I and BamHI were introduced into the --

Column 7, line 39, reads "NO: 1) was introduced near the BcII and BamHI linkage site"
    should read -- NO: 1) was introduced near the Bc/I and BamHI linkage site --

Column 7, line 54, reads "BcII and BamHI and treated with equal volume of phenol,"
    should read -- Bc/I and BamHI and treated with equal volume of phenol, --

Column 7, line 55, reads "followed by centrifugation at 12000 rpm for 5 mm. The"
    should read -- followed by centrifugation at 12000 rpm for 5 min. The --

Column 7, line 59, reads "c) The digested product was ligated to vector VR1012"
    should read -- c) The digested product was ligated to vector VR1 012 --

Column 7, line 60, reads "(Vical Inc.) which had been digested with same enzymes, and"
    should read -- (Vical Inc.) which had been digested with the same enzymes, and --

Column 7, line 67, reads "vector VR1012."
    should read -- vector VR1 012 --

Column 8, line 4, reads "falciparfum"
    should read -- falciparum --

CERTIFICATE OF CORRECTION (continued)
U.S. Pat. No. 7,981,601 B2

Column 8, line 11, reads "conjunction with a Hind/III site. Briefly, for the randomiza-"
should read -- conjunction with a HindIII site. Briefly, for the randomiza- --

Column 8, line 15, reads "aliquots. One was cleaved with BC/I and Hind/III the other"
should read -- aliquots. One was cleaved with BC/I and HindIII, the other --

Column 8, line 16, reads "with BamHI and Hind/III. And the fragments from the two"
should read -- with BamHI and HindIII. And the fragments from the two --

Column 8, line 64, reads "C., 3 mm 94 C., 30 sec; 50 C., 30 sec; 72 C., 30 sec; 30"
should read -- C., 3 min 94 C., 30 sec; 50 C., 30 sec; 72 C., 30 sec; 30 --

Column 9, line 1, reads "VR1O12 which had been cleaved with EcoRV and BC/I, and"
should read -- VR1 012 which had been cleaved with EcoRV and Bc/I, and --

Column 9, line 19, reads "Chimeric Genes of Plasmodium falciparfum"
should read -- Chimeric Genes of Plasmodium falciparum --

Column 9, line 28, reads "The PCR product was cleaved with bc/I and BamHI and"
should read -- The PCR product was cleaved with Bc/I and BamHI and --

Column 10, line 13, reads "the gel for at least 20 mm with horizontally shaking slowly."
should read -- the gel for at least 20 min with horizontal shaking slowly. --

Column 10, line 54, reads "from OD250/OD280 measured with DU7O ultraviolet spectro-"
should read -- from OD250/OD280 measured with DU70 ultraviolet spectro --

Column 11, line 26, reads "and 100 ul of the diluted antisera with each concentration in"
should read -- and 110 ul of the diluted antisera with each concentration in --

Column 12, lines 1-2, read "1) Recognition of Native Proteins of Plasmodium falcipar-
fum"
should read --1) Recognition of Native Proteins of Plasmodium par-
um --

Column 12, lines 3-4, read "a) Blood cells with erythrocytic stage Plasmodium falci-
parfum 3D7 (or FCC1) (with an infection rate of about 2%)"

should read -- a) Blood cells with erythrocytic stage Plasmodium falci-
parum 3D7 (or FCC1) (with an infection rate of about 2%) --

Column 12, line 33, reads "native proteins of Plasmodium falciparfum in above section"
should read -- native proteins of Plasmodium falciparum in above section --

CERTIFICATE OF CORRECTION (continued)
U.S. Pat. No. 7,981,601 B2

Column 12, line 38, reads "Plasmodium falciparfum by the antisera generated by the"
    should read -- Plasmodium falciparum by the antisera generated by the --

Column 12, line 42, reads "from the Spanin-treated Plasmodium falciparfum. Poly-"
    should read -- from the Spanin-treated Plasmodium falciparum. Poly- --

Column 12, line 50, reads "of Plasmodium falciparfum strain 3D7 was collected by cen-"
    should read -- of Plasmodium falciparum strain 3D7 was collected by cen- --

Column 14, line 40, reads "of cytokine CD8, wherein positive polyepitope gene 5P312"
    should read -- of cytokine CD8, wherein positive polyepitope gene SP312 --

Column 14, line 42, reads "5P352 or SP462. In contrast, negative polyepitope genes"
    should read -- SP352 or SP462. In contrast, negative polyepitope genes --

Column 14, line 43, reads "behaved similar to empty vector, demonstrating that poly-"
    should read -- behaved similarly to empty vector, demonstrating that poly --

Column 34, line 57, reads "a) selecting, synthesizing and cloning Into a vector a plu-"   (Claim 10)
    should read -- a) selecting, synthesizing and cloning into a vector a plu- --

Column 35, lines 21-22, reads "13. The method according to claim 1, wherein the ran-   (Claim 13)
domly assembling of the polyepitope chimeric genes with"

should read --13. The method according to claim 1, wherein the random
    assembling of the polyepitope chimeric genes with --

Column 36, lines 10-11, reads "16. The method according to claim 10, wherein the ran-   (Claim 16)
domly assembling of the polyepitope chimeric genes with"

should read --16. The method according to claim 10, wherein the random
    assembling of the polyepitope chimeric genes with --

Column 36, line 12, reads "different lengths in step c) is carried out simultaneously by"   (Claim 16)
    should read -- different lengths in step c) is carried out simultaneously by the --